United States Patent
D'Amore et al.

(10) Patent No.: US 11,680,341 B2
(45) Date of Patent: Jun. 20, 2023

(54) MANDREL-LESS ELECTROSPINNING PROCESSING METHOD AND SYSTEM, AND USES THEREFOR

(71) Applicants: University of Pittsburgh—Of the Commonwealth System of Higher Education, Pittsburgh, PA (US); Ri.MED Foundation, Palermo (IT)

(72) Inventors: Antonio D'Amore, Pittsburgh, PA (US); William R. Wagner, Gibsonia, PA (US)

(73) Assignees: University of Pittsburgh—Of the Commonwealth System of Higher Education, Pittsburgh, PA (US); Ri.MED Foundation

(*) Notice: Subject to any disclaimer, the term of this patent is extended or adjusted under 35 U.S.C. 154(b) by 822 days.

(21) Appl. No.: 16/494,797

(22) PCT Filed: Mar. 16, 2018

(86) PCT No.: PCT/US2018/022863
§ 371 (c)(1),
(2) Date: Sep. 17, 2019

(87) PCT Pub. No.: WO2018/175234
PCT Pub. Date: Sep. 27, 2018

(65) Prior Publication Data
US 2020/0010979 A1 Jan. 9, 2020

Related U.S. Application Data

(60) Provisional application No. 62/473,588, filed on Mar. 20, 2017.

(51) Int. Cl.
A61F 2/24 (2006.01)
D01D 5/00 (2006.01)
A61L 27/18 (2006.01)

(52) U.S. Cl.
CPC ......... *D01D 5/0076* (2013.01); *A61F 2/2457* (2013.01); *A61L 27/18* (2013.01); *A61F 2240/001* (2013.01); *A61L 2430/20* (2013.01)

(58) Field of Classification Search
CPC ............... D01D 5/0076; A61F 2/2457; A61F 2240/001; A61F 2/2415; A61L 27/18;
(Continued)

(56) References Cited

U.S. PATENT DOCUMENTS 4,689,186 A 8/1987 Bornat
5,216,115 A 6/1993 Kohn et al.
(Continued)

FOREIGN PATENT DOCUMENTS

WO 2012024390 A2 2/2012
WO 2016138416 A1 9/2016
WO 2016138423 A1 9/2016

OTHER PUBLICATIONS

Iung et al., "A prospective survey of patients with valvular heart disease in Europe: The Euro Heart Survey on Valvular Heart Disease", European Heart Journal, 2003, pp. 1231-1243, vol. 24.
(Continued)

*Primary Examiner* — Suzette J Gherbi
(74) *Attorney, Agent, or Firm* — The Webb Law Firm

(57) ABSTRACT

A system and method are provided for manufacturing filamentous polymer matrices, comprising electrospinning a polymer fiber into a gap between two or more spaced-apart electrodes.

20 Claims, 11 Drawing Sheets

(58) Field of Classification Search
CPC ............. A61L 2430/20; A61L 2400/12; A61L 2430/10; A61L 27/56; A61L 27/58
See application file for complete search history.

(56) References Cited

U.S. PATENT DOCUMENTS

| | | | |
|---|---|---|---|
| 8,211,352 B2* | 7/2012 | Baca | D01D 5/0076 264/484 |
| 9,833,315 B2* | 12/2017 | Vidlund | A61L 33/0011 |
| 10,092,676 B2 | 10/2018 | Amoroso et al. | |
| 2002/0173213 A1 | 11/2002 | Chu et al. | |
| 2002/0175449 A1 | 11/2002 | Chu et al. | |
| 2003/0113481 A1* | 6/2003 | Huang | C23C 14/228 427/580 |
| 2008/0237934 A1 | 10/2008 | Reneker et al. | |
| 2008/0260831 A1 | 10/2008 | Badylak et al. | |
| 2011/0018174 A1* | 1/2011 | Baca | D01D 5/0092 425/174.8 E |
| 2011/0082545 A1 | 4/2011 | Freund | |
| 2016/0325013 A1 | 11/2016 | Li et al. | |
| 2016/0331527 A1* | 11/2016 | Vidlund | A61L 33/0011 |
| 2018/0071087 A1 | 3/2018 | Badhwar et al. | |
| 2018/0071088 A1 | 3/2018 | Badhwar et al. | |
| 2018/0228937 A1* | 8/2018 | Jin | A61L 27/18 |
| 2020/0002828 A1* | 1/2020 | Mills | H01L 31/0725 |

OTHER PUBLICATIONS

Koch et al., "A Custom Image-Based Analysis Tool for Quantifying Elastin and Collagen Micro-Architecture in the Wall of the Human Aorta from Multi-Photon Microscopy", J Biomech, 2014, pp. 935-943, vol. 47:5.

Stankus et al., "Hybrid nanofibrous scaffolds from electrospinning of a synthetic biodegradable elastomer and urinary bladder matrix", J Biomater Sci Polym Ed, 2008, pp. 635-652, vol. 19:5.

Teo et al., "Electrospun fibre bundle made of aligned nanofibres over two fixed points", Nanotechnology, 2005, pp. 1878-1884, vol. 16.

* cited by examiner

MANDREL-LESS ELECTROSPINNING PROCESSING METHOD AND SYSTEM, AND USES THEREFOR

CROSS REFERENCE TO RELATED APPLICATIONS

This application is the United States national phase of International Application No. PCT/US2018/022863 filed Mar. 16, 2018, claims the benefit of U.S. Provisional Patent Application No. 62/473,588 filed Mar. 20, 2017, each of which is incorporated herein by reference in its entirety.

A variety of electrodeposition or electrospinning processes are known—each having its strengths and limitations. Current commercial products for heart valve chordae tendineae replacement are based on conventional surgical suture materials which are typically categorized into two families: non-degradable and degradable. Non-degradable suture materials include: polypropylene, prolene, polyamide, polyester, silk, steel. Most common degradable surgical suture materials include: polyglactin, polyglycolic acid, catgut, poliglecaprone, polydioxanone. Regardless of their capacity to be reabsorbed, these materials currently used as chordae substitutes are characterized by solid cross-sections, do not recapitulate the native micro-architecture nor the mechanics, as such they do not allow for endogenous formation of functional tissue. This limitation significantly reduces the efficacy of these materials as viable candidates for chordae/valve repair and replacement. Issues directly associated include mechanical mismatch at the papillary muscles, tissue failure, and foreign body response.

The adjusted prevalence for valvular disease in US is estimated as 2.5% with nearly 50,000 deaths reported in year 2013. Among these, more than 25% are related to mitral valve regurgitation or stenosis and might involve damage to one or several chordae tendineae. For instance, in one study, 46.5% of the mitral valve regurgitation cases involved one or multiple chordae repair operations (lung B, et al. A prospective survey of patients with valvular heart disease in Europe: The Euro Heart Survey on Valvular Heart Disease. European Heart Journal. 2003; 24:1231-43).

While technology has evolved in terms of surgical strategies and tools to position and suture chordae tendineae, engineering of the chorda tendineae remained largely unexplored. Potential benefits deriving from an effective technique to create artificial (prosthetic) biodegradable tendineae include: physiological mechanics, improved structural integrity and longevity, endogenous tissue growth with consequent enhanced biocompatibility, fibrillar, porous materials with fibers perpendicular to the cross section—as opposed to solid materials—and the capacity to combine this technology with stentless polymeric heart valves (see, e.g., International Patent Application Publication Nos. WO 2016/138416 and WO 2016/138423).

SUMMARY

According to one aspect of the invention, a mandrel-less electrodeposition system for use in preparing a filament is provided. The system comprises: two or more static or rotating target electrodes having opposing, spaced-apart tips electrically-connected to an electrical power source, the opposing tips of the electrodes defining a deposition target axis; a nozzle electrically-connected to a second electrical power source and spaced apart from the target electrodes and the deposition target axis; and a reservoir configured to deliver a polymer composition through the nozzle and to the deposition target axis.

According to another aspect of the invention, a method of making a filament is provided. The method comprises: feeding a first polymer composition through a first nozzle having a first electrical charge into a target deposition axis defined by spaced-apart tips of a first target electrode and a second target electrode, the first and second target electrodes having a different electrical charge from the first electrical charge that produces an electric field (voltage gap) that causes fibers of the polymer composition to align along the target deposition axis between the target electrodes, thereby forming a primary filament between the target electrodes.

BRIEF DESCRIPTION OF THE DRAWINGS

FIG. 6A. SEM images and details of the post processing of posterior basal chordae tendineae, as compared to FIG. 6B. FIG. 6B. PEUU engineered chorda. PEUU fibers showed morphology and scale comparable to native chordae tendineae. FIG. 6C. Fiber orientation was quantified by the method reported in Koch, R. et al. (R. Koch, et al., A Custom Image-Based Analysis Tool for Quantifying Elastin and Collagen Micro-Architecture in the Wall of the Human Aorta from Multi-Photon Microscopy. Journal of Biomechanics 2014, 47, (5), 935-943). FIG. 6D. Fiber network orientation index of engineered chordae showed values comparable with the native porcine chordae tendineae.

FIG. 8A. Ultimate tensile testing stress; FIG. 8B. strain at break; FIG. 8C. elastic modulus; FIG. 8D. initial elastic modulus.

DETAILED DESCRIPTION

Figure 1:
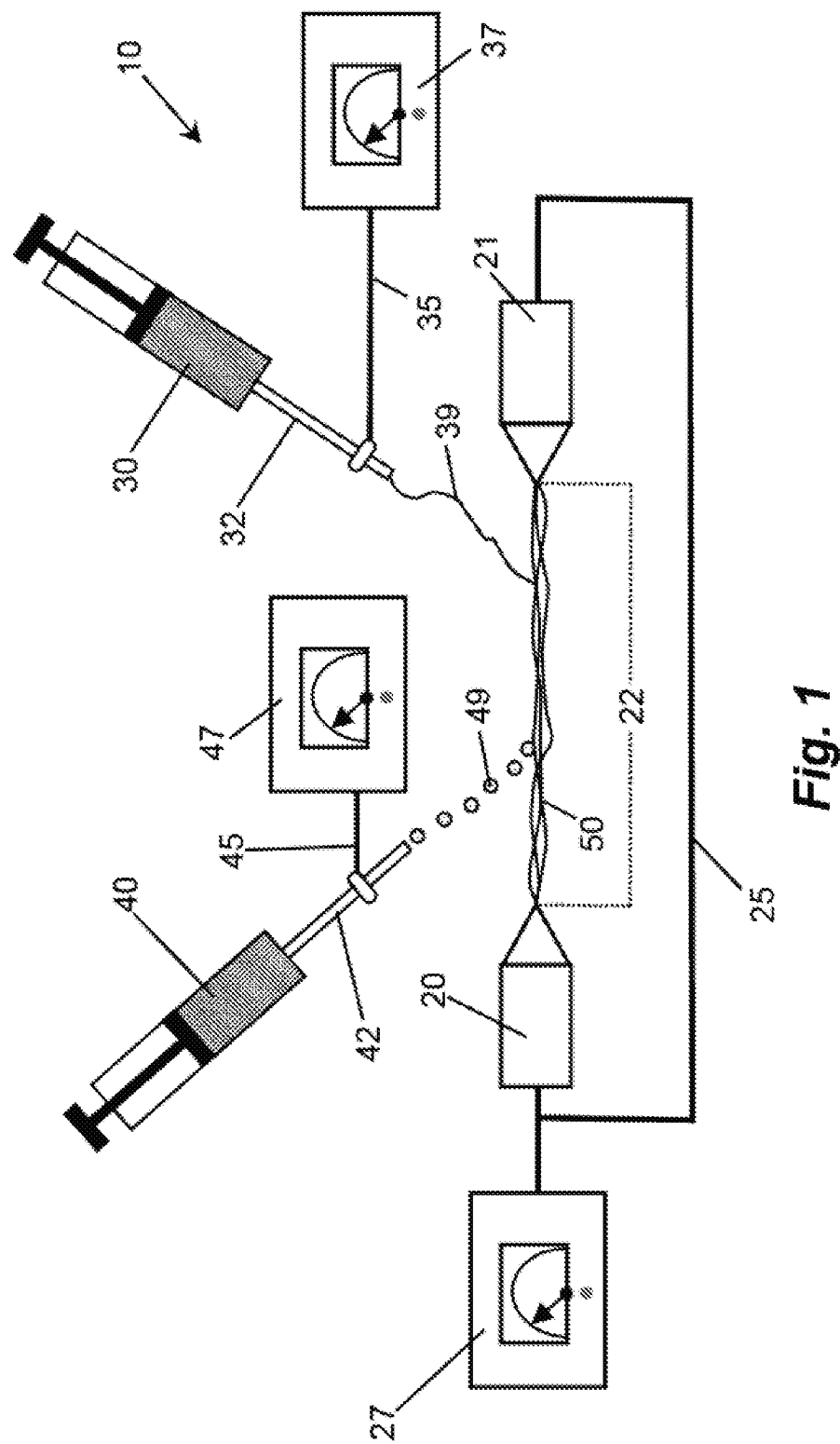
FIG. 1: Schematic of a mandrel-less electrospinning set up with processing variables for engineered chorda tendineae fabrication.

The use of numerical values in the various ranges specified in this application, unless expressly indicated otherwise, are stated as approximations as though the minimum and maximum values within the stated ranges are both preceded by the word "about." In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the terms "comprising," "comprise" or "comprised," and variations thereof, are meant to be open ended. The terms "a" and "an" are intended to refer to one or more.

As used herein, the term "target" refers to points, surfaces or volumes in space influenced by the presence of an electrical charge or field to which polymer composition migrates and is deposited during the course of electrodeposition. In the context of the present disclosure, through use of two target electrodes, the target is the deposition axis produced by the two target electrodes.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc., for example repairing chordae tendineae.

A "prosthetic" article is a synthetic (artificial, or man-made) article that replaces an indicated body part, either temporarily or permanently, such as a chordae tendineae, a tendon, or a ligament. For example and without limitation, a prosthetic chordae tendineae is a synthetic chordae tendineae structure that either permanently or temporarily replaces, or otherwise stands in for, a natural chordae tendineae or a portion thereof. In aspects, if the prosthetic article degrades (bioerodes) over time, it includes, at least in part, a bioerodible portion that optionally may be replaced by nascent tissue over time, for example, by growth or differentiation of cells implanted within or on the article, or by growth or differentiation of cells that migrated into and/or onto the article, thereby forming nascent tissue, such as a nascent chordae tendineae.

As used herein, the term "patient" or "subject" refers to members of the animal kingdom including but not limited to human beings and "mammal" refers to all mammals, including, but not limited to human beings.

As used herein, the terms "cell" and "cells" refer to any types of cells from any animal, such as, without limitation, rat, mouse, monkey, and human. For example and without limitation, cells can be progenitor cells, e.g. pluripotent cells, including stem cells, induced pluripotent stem cells, multi-potent cells, or differentiated cells, such as endothelial cells and smooth muscle cells. In certain aspects, cells for medical procedures can be obtained from the patient for autologous procedures, or from other donors for allogeneic procedures. Methods of identifying, isolating and preparing cells, including stem cells and induced stem cells, are broadly-known.

A "cell growth scaffold" is a mesh, matrix, particle, surface, or other material upon which or into which a cell can be deposited and can be maintained in a living state, and often propagates (multiplies) in the presence of a cell growth medium.

A polymer composition is "biocompatible" in that the polymer composition and, where applicable, degradation products thereof, are substantially non-toxic to cells or organisms within acceptable tolerances, including substantially non-carcinogenic and substantially non-immunogenic, and are cleared or otherwise degraded in a biological system, such as an organism (patient) without substantial toxic effect. For biodegradable polymers, non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g., terminal groups, that are modified during polymerization are changed, removed, and/or relocated, and certain bonds may be added, removed, and/or modified. A monomer may be a "macromer", an oligomer or polymer that is the combination product of two or more smaller residues, and is employed as a monomer in preparation of a larger polymer. An incorporated monomer is referred to as a "residue" of that monomer.

A "moiety" is a portion of a molecule, compound or composition, and includes a residue or group of residues within a larger polymer.

A polymer is said to comprise a specific type of linkage if that linkage is present in the polymer, thus, a polyester comprises a plurality of ester linkages, a polyurethane comprises a plurality of urethane (e.g., carbamate) linkages, and a poly(ester urethane) urea comprises ester, urethane, and urea linkages. Unless otherwise specified, molecular weight for polymer compositions refers to weight average molecular weight ($M_W$). Composition of a copolymer may be expressed in terms of a ratio, typically a molar ratio, of incorporated monomers or as a feed ratio of monomers prior to polymerization. In the case of feed ratios, the relative amount of each monomer incorporated into the copolymer is influenced by reaction kinetics, and the nature of the chemical reaction(s) employed to join the monomers.

As described herein, a "fiber" is an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers produced by traditional electrospinning) and can be isotropic or anisotropic. A "filament" is an article comprising one or more fibers.

The term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions, described herein. Biological polymers can be chemically modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of chordae tendineae repair, it is desirable that the matrix dissolves over at least a week and preferably longer. More importantly, the matrix would have to retain its supportive capacity until tissue remodeling occurs, such as for at least 2-8 weeks, or longer. Biodegradable articles completely degrade in vivo within two years, and in many instances within one year.

As used herein, the term "derive" and any other word forms or cognates thereof, such as, without limitation, "derived" and "derives", refers to a component or components obtained from any stated source by any useful method.

Provided herein are methods and devices useful for preparing electrospun articles, for example and without limitation, prosthetic chordae tendineae. The technology is useful broadly for preparation of fibers and fiber-like tissue, including tendons and ligaments for orthopedic and dental applications, such as for periodontal ligaments, with engineered constructs lengths reaching up to 6 through 10 cm and fiber diameter being a linear function of the deposition time (e.g., 5 minutes of deposition produce chords of 1.1 mm in diameter). While the methods and systems described herein are useful for engineering tissues, with use of biodegradable materials, they also can be utilized to form non-degradable biomaterials, and materials other than tendons, or ligaments, or even for manufacture of non-implantable articles. While being particularly suited for preparation of articles useful for tissue engineering, e.g., for production of engineered chordae tendineae, the articles prepare by the methods, devices, and systems described herein can be used for any purpose.

In the context of prosthetic chordae tendineae (artificial chordae tendineae), in mandrel-targeted electrospinning, mechanical properties of the devices are of two orders of magnitude lower than native chordae and are heavily affected by collagen shrinkage. The methods and systems described herein overcome these limitations—introducing a novel mandrel-less design capable of fabricating electrospun chordae tendineae with 1) physiologically relevant mechanical properties, 2) high surface area and porosity essential for cell attachment and proliferation, 3) elastomeric nature suitable for in vitro mechanical conditioning and subsequent mechanical properties enhancement. Benefits of the methods and systems described herein include, in aspects: mandrel-less deposition: innovative micro-fibers deposition modality with potential applications for cardiac, orthopedic, dental tissue engineering, and for other material, e.g., for filaments, threads, polymeric wire, and cable processing; capacity to generate biomimetic tendon or ligament surrogates with physiological structure and mechanics; control over the construct cross section; control over micro-fiber cross section; possibility to incorporate multiple polymer streams, cells, extracellular matrix (ECM) products, cell culture medium, blood products, and/or growth factors to facilitate seeding, cell proliferation and de-novo ECM elaboration; ability to fabricate macroscopic chordae with native-like multiple branches; ability to combine this technology with other prosthetics, e.g. polymeric prosthetics, for example, as disclosed in International Patent Application Publication Nos. WO 2016/138416 and WO 2016/138423, e.g., by attaching the constructs to polymeric valve leaflets; ability to incorporate degradable and non-degradable materials; and translation of the methods described herein to produce filaments useful for medical or veterinary purposes, or for non-medical or veterinary purposes.

Therefore, provided herein are branched or unbranched filaments or polymeric articles, such as prosthetic tissues and filaments, useful, for example and without limitation, in medical procedures, such as heart and heart valve repair, or wound healing or repair. In one aspect, the filaments serve as a prosthetic tendon, such as chordae tendineae, which can be attached in place by any useful means, such as by suturing, stapling, or gluing, and optionally attached to other prosthetic articles, such as a prosthetic heart valve, for example, as described in International Patent Application Publication No. WO 2016/138416, incorporated herein by reference for its technical disclosure of prosthetic heart valves and methods of making prosthetic heart valves.

FIG. 1 depicts one aspect of a system 10 as described herein. As depicted in FIG. 1, system 10 includes a first electrode 20 and a second electrode 21 defining a gap 22 between the first and second electrode 20 and 21. In one aspect, the gap 22 between the first electrode 20 and the second electrode 21 is 5 cm. Electrodes 20 and 21 are electrically connected, via a lead 25, to a power supply 27. The system 10 also includes a first syringe 30, comprising a first nozzle 32. A lead 35 is attached to the first nozzle 32, electrically connecting the first nozzle 32 to a second power supply 37. A polymer microfiber 39 is shown being electrodeposited (e.g., electrospun) from the first syringe 30 via the first nozzle 32. The system 10 also includes a second syringe 40, comprising a second nozzle 42. A lead 45 is attached to the second nozzle 42, electrically connecting the nozzle 42 to a third power supply 47. Liquid droplets 49 are shown being electrodeposited (e.g., electrosprayed) from the second syringe 40 via the second nozzle 42 for wet deposition of the polymer microfibers 39 to form a fiber matrix 50. The polymer microfibers 39, and the liquid droplets 49 combine along an axis defined by the electrodes 20 and 21, to form the fiber matrix 50, as depicted. Liquids deposited by the second nozzle 42 for wet fabrication methods for depositing liquids, include, without limitation, saline, phosphate-buffered saline (PBS), cell media, blood products (e.g., serum, plasma, or platelet-rich plasma), cells, therapeutic compositions, solubilized ECM, or any other useful liquid to be deposited onto nascent electrospun polymer fibers or filaments. The system 10 does not necessarily include or require a second system for depositing a liquid and, therefore, only optionally includes the second syringe 40, the second nozzle 42, the lead 45, and the third power supply 47. The first, second, and optional third power supplies 27, 37, and 47, are independently controllable so that their output can be independently adjusted to permit optimization of electrodeposition of the components of the fiber matrix 50.

The electrical and mechanical elements of the systems and methods described herein may be selected, combined, and/or optimized by a person of ordinary skill, and therefore can be represented in a large variety of physical and circuit structures. Leads as described herein are electrical conductors, and can comprise any suitable material and topological configuration for conducting an electric current, such as a wire or a conductive trace, or combinations of connectors. Further, electric circuit elements, such as, without limitation, leads or electrodes can comprise additional components, such as LEDs, switches, resistors, capacitors, diodes, transistors, integrated circuits (IC), or other electric or electronic elements, as are broadly-known in the art. Control circuits and devices can have any useful structure or topology and can comprise digital and/or analog control elements. Power supplies, controls, as well as other elements of the system may be housed individually, or all or some of the elements of the system can be housed together in an integrated housing or structure, as is within the skill of an electrical engineer with ordinary skill in the art.

The syringes 30 and 40 depicted in FIG. 1 are be used to deliver polymer (first syringe 30) and, optionally another liquid (second syringe 40). The nozzles are depicted in a specific orientation relating to the electrodes, but in practice can be placed in any suitable spatial location such as normal to the deposition axis extending between the two electrodes, and typically in an optimized spatial location. Although syringes, such as medical syringes, are depicted, any reservoir, nozzle, and fluid pumping apparatus can be employed, including peristaltic pumps, medical syringes, gravity-feed systems, etc. as are broadly-known. Likewise, nozzles can be any suitable size and shape conductor, including, without limitation, standard medical hypodermic needles, or metal tubes. Deposition and control of the rate of deposition of the polymer or other liquid can be manual, though for reproducibility and uniformity, deposition control is automated. For example, in one aspect, deposition is controlled by syringe pumps, such as programmable syringe pumps, as are broadly-known in the laboratory and medical arts. Control of deposition can be programmed into the syringe pump, or can be controlled by a separate computing unit, such as a personal computer, workstation, smartphone, etc. Syringe and syringe pumps are one method of delivering controlled amounts of polymer and, where applicable, other liquids, in the described system. In another aspect, referring to the system 10 depicted in FIG. 1, rather than syringes 30 and 40, a peristaltic pump, or an infusion pump, is used to control delivery of the polymer and, where applicable, other liquids. Choice of an appropriate delivery mechanism for the polymer and, where applicable, other liquid(s), is well-within the abilities of a person of ordinary skill in the engineering arts. Further, additional sources of other polymers, or other constituents, such as ECM material, useful in preparation of a fiber matrix, may be added, and electrodeposited under suitable conditions.

In further reference to FIG. 1, and equally applicable to other systems described herein, the parameters, such as voltage, distance between a pair of target electrodes, distance between nozzles, distance between nozzles and an axis between tips of the electrodes, etc., are exemplary and are provided for illustrative purposes. The power supplies can be individual as shown (e.g., referring to the system depicted in FIG. 1, 10 kV for the first power supply 27, −5 kV for the second power supply 37, and 8 kV for the third power supply 47), or integrated into a single housing.

In use, one or more, or all, of the nozzles and electrodes are spatially positioned using a manual or automatic positioning system, such as X-Y or X-Y-Z stages, or other robotics, as are broadly-known. The nozzles and electrodes may be positioned statically during the entire electrospinning process, or may be moved relative to each other or rotated during the process, for example, to ensure uniform deposition over the entire electrospun article, or to produce thicker, thinner, or in a broader sense, different, regions in the electrospun article.

In one aspect, the target electrodes rotate about the deposition axis between tips of the target electrodes, and in one aspect synchronously—that is, at the same angular velocity such that the deposited fibers rotate along a longitudinal axis, thereby facilitating even deposition of the polymer. In another aspect, the target electrodes rotate about the deposition axis asynchronously, producing a twist in the fiber as formed. The relative rotation of the two electrodes can be controlled, e.g., computer-controlled, over the course of electrodeposition to produce a complex pattern of twisting, such as a twisted center of the deposited fiber surrounded by an un-twisted, or differently-twisted outer layer. As with positioning, rotation of the target electrodes, independently or with a single motor, can be accomplished using motors and belts, gears, or any suitable method as is known in the art.

The target electrodes can be prepared from any suitable conductive material, such as aluminum, copper, steel, iron, silver, gold, platinum, carbon/graphite, titanium, etc., and any alloy or composite structure, such as brass or bronze, that can serve as an electrode. The target electrodes have a tip that can be pointed, rounded, flat or have any suitable shape—so long as it has a small, e.g., less than 5 mm, 4 mm, 3 mm, 2 mm, or 1 mm in diameter, such as its largest diameter normal to the deposition axis (extending between opposing electrode tips). Thus, the electrode typically is cylindrical or tapers to the tip.

Figure 2:
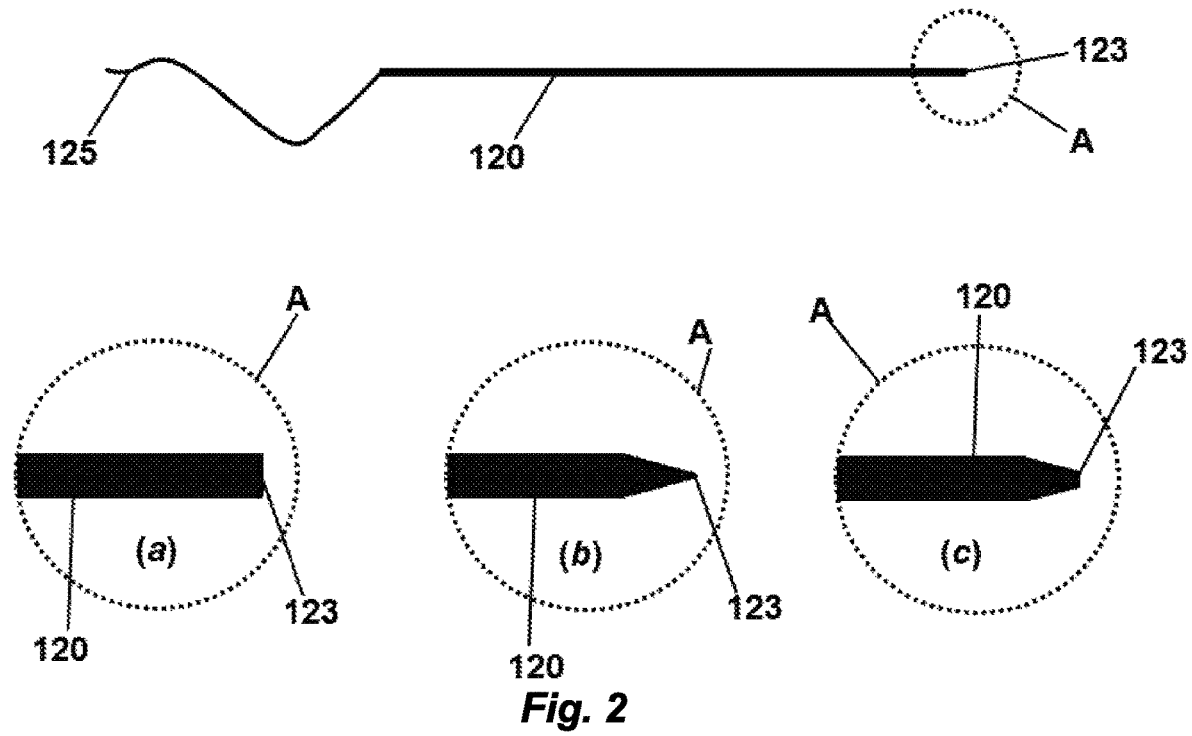
FIG. 2 is a diagram of a needle electrode according to one aspect of the invention.

Referring to FIG. 2, a cylindrical needle electrode 120 is depicted, having a tip 123 and lead 125, such as a wire or trace, for electrically-connecting the needle electrode 120 to a power supply. Variation on the shape of the tip 123 (expanded view A) are shown in (a) (flat tip), (b) (conical tip), and (c) (frustoconical tip). In aspects, portions of the needle electrode 120 other than the tip optionally are covered with an insulator. The needle electrode 120 can be used as a target electrode, or as a secondary electrode for use in preparing a branched article. By "needle electrode", it is meant an electrode having a tip and adjacent portion of small diameter, such as an inflexible or flexible rod or wire that is substantially cylindrical and typically has a diameter of less than 1 mm, permitting in the context of the present invention, locating the tip of the electrode within a nascent filament formed between two target electrodes. The above-described process may be repeated to add additional branches, such as 1, 2, 3, 4, 5, etc. branches in addition to the main fiber.

Figure 3:
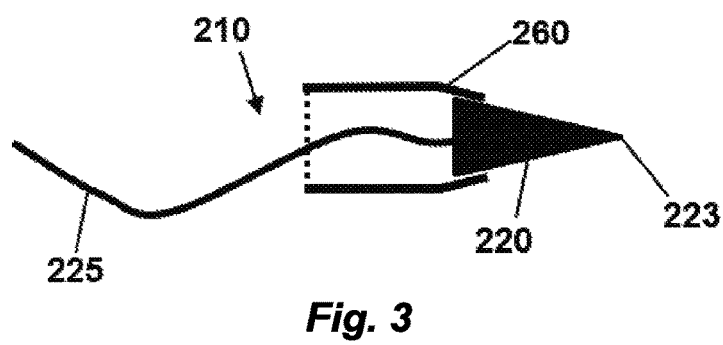
FIG. 3 depicts a target electrode according to one aspect of the invention.

FIG. 3 depicts schematically an electrode 220 having a tip 223, lead 225, which can be a wire or a trace, and insulator 260. As above, the electrode 220 is a conductor, and can be made from any suitable conductive material. Electrode 220 can have any suitable shape, and tip configuration as described above, and for example and without limitation, conical with a pointed tip, frustoconical with a flat tip, pyramidal with a pointed tip, bullet-shaped with pointed tip, bullet-shaped with flat or rounded tip, polygonal tapered with pointed tip, or irregular tapered shape with pointed tip. As would be appreciated by those of ordinary skill, the electrode size and shape can be varied greatly, though it should be tapered to a small diameter tip if, as in the case of the needle electrode, the diameter of the electrode is sufficiently small (e.g., less than 5, 4, 3, 2, or 1 mm) so as to facilitate deposition of filaments of varying thickness as described herein.

Electrodeposition, e.g., electrospinning, is used to deposit the polymer composition and, optionally, the ECM gel and/or other liquid, gel, cell or other biological or therapeutic constituents, such as a mammalian blood product, media buffer solution, medium, drug products, antibodies, etc. In its simplest sense, electrodeposition is caused by the deposit of a liquid composition, such as polymer fibers in the case of electrospinning, onto a target surface in the case of a single electrode and/or to a deposition axis or space created by and between spatially-distanced electrodes. Electrospinning methods are well-known in the field of tissue engineering and are conducted essentially as described below. Electrospinning permits fabrication of structures that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy, or structures having varying anisotropy at different parts of the structure. These aligned structures can influence cellular growth, morphology and ECM production.

The process of electrospinning involves placing a polymer-containing fluid (for example, a polymer solution, a polymer suspension, or a polymer melt) in a reservoir equipped with a small orifice, such as a needle, pipette tip, metal tube, or other metal structure referred to herein as a nozzle and also can be referred to as a spinneret, and a metering pump, such as a syringe pump or a peristaltic pump. One electrode of a high voltage source is placed in electrical contact with the polymer-containing fluid or orifice, while another electrode is placed in electrical contact with a target (traditionally, typically a collector screen or rotating mandrel), and in the context of the present invention, two spaced-apart electrodes that produce a target deposition axis in the space between the two electrodes, or even multiple spaced-apart electrodes that produce a target deposition space in the space between the electrodes in a pattern dictated by the relative position of the electrodes and electrical field produced by the electrodes.

During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically-shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, target deposition axis or target deposition space, which typically is biased (electrically-charged) so that the total voltage difference between the nozzle and the target is sufficiently large to cause effective electrodeposition, e.g., 20 kV, though other potentials and polarities are able to achieve effective electrodeposition, for example, between −2 and −20 kV. Optionally, a focusing ring with an applied bias (for example, 1 to 10 kV) can be used to direct the trajectory of the charged jet of polymer-containing fluid. Under certain conditions, for instance with solutions lacking sufficient viscosity and/or electrospun with certain tolerances, a fiber is not formed, but a spray is formed, depositing discrete droplets onto the target instead of a fiber. This is electrospraying.

Relative charges of the nozzle and electrodes may be the reverse polarity (e.g., with the target, target deposition axis or target deposition space, which typically is biased (electrically charged) between 2 to 10 kV, and the nozzle being charged between from −3 to −15 kV). As the charged jet of fluid travels towards the biased target, target deposition axis or target deposition space, the solvent typically evaporates during mid-flight, leaving behind a polymer fiber on the biased target, at the target deposition axis, or within the target deposition space. If the fluid is a polymer melt, the molten polymer cools and solidifies in mid-flight and is collected as a polymer fiber on the biased target, at the target deposition axis, or within the target deposition space. As the polymer fibers accumulate on the biased target, at the target deposition axis, or within the target deposition space, a non-woven, porous mesh is formed.

The systems and devices described herein are described as mandrel-less, meaning they are configured to, or adapted to, produce an electrospun article in a gap or space defined by two, three, or more, spaced-apart target electrodes, and not wholly onto a physical target surface, such as a rotating mandrel, as with conventional electrodeposition processes. The electrospun fibers of a mandrel-less system accumulate in the space between the spaced-apart target electrodes and span the gap between those electrodes, forming a fiber matrix attached to the electrodes and extending into a space between the electrodes, thereby connecting the electrodes.

The properties of the electrospun structures, e.g., elastomeric scaffolds, can be tailored by varying the electrospinning conditions. For example, when the biased target, target deposition axis, or target deposition space is relatively close to the orifice, the resulting electrospun mesh tends to contain unevenly thick fibers, such that some areas of the fiber have a "bead-like" appearance. However, as the biased target, target deposition axis, or target deposition space is moved further away from the orifice, the fibers of the non-woven mesh tend to be more uniform in thickness. Moreover, the biased target, target deposition axis, or target deposition space can be moved relative to the orifice to create different qualities of the article depending on the relative locations of the nozzle and the target, target deposition axis or target deposition space.

In the context of the present invention, due to the electrical field created by two or more spaced-apart target electrodes, fibers of the non-woven mesh are oriented (therefore, anisotropic) towards the direction of the axis of deposition between the tips of the electrodes. In this instance, the resulting non-woven mesh filament may have a higher resistance to strain in the direction parallel to the fibers, compared to the direction perpendicular to the fibers making the resultant article particularly suited for use as prosthetic tendons, ligaments, or as filaments in general. The properties of the electrospun structure may also be varied by changing the magnitude of the voltages applied to the electrospinning system. In one exemplary and non-limiting aspect, the electrospinning apparatus includes a nozzle biased to 12 kV, a target electrodes biased to −7 kV each, and one or more optional nozzles biased to 3-10 kV to allow for concurrent electrospinning of different polymer compositions, or electrospray of cell solutions, ECM material, liquids, liquids comprising therapeutic agent(s), blood products, etc. Examples of useful orifice diameters range from 0.1 to 2 mm (I.D.) and a useful target distances (distance from nozzle to axis of deposition) range from 1 to 17 cm. Other electrospinning conditions that can be varied include, for example and without limitation, the feed rate of the polymer solutions, the solution concentrations, the polymer molecular weight, the injectors-deposition target axis distance, as well as the nozzle-target axis relative positioning and trajectories, e.g., controlled via robotic control systems.

As indicated above, in certain examples, electrospinning is performed using two or more nozzles, wherein each nozzle is a source of a same or different polymer solution. The nozzles may be biased (electrically charged) with different biases or the same bias in order to tailor the physical and chemical properties of the resulting fiber matrix.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In one non-limiting example, the structure is produced by co-electrospinning a polymer suspension comprising a synthetic polymeric component and a biological polymeric component, along with electrospraying an ECM gel and/or other liquid(s). In another non-limiting example, the polymeric component of the structure is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

If present, an ECM gel component of the structure is sprayed (e.g., pressure sprayed) or electrosprayed concurrently with the electrospinning of the polymer(s). Likewise, the liquid component of the wet-electrospun layer(s) is sprayed or electrosprayed concurrently with the polymeric constituents.

The articles described herein are prepared from any natural or synthetic biocompatible, electrodepositable material. In certain illustrative examples below, the filaments are prepared from a urethane, for example, and without limitation, a poly(ester-urethane)urea (PEUU), which is synthesized using putrescine as a chain extender and two-step solvent synthesis method described. PEUU features include high elasticity and mechanical strength coupled with controllable biodegradative and cell-adhesive properties. The polymer composition has found use in a number of in vivo scenarios including as a cardiac patch, in prosthetic heart valves, in abdominal wall repair, and in vascular grafts. Alternative chemistries allow the polyurethanes to include added non-thrombogenic chemical moieties, and to use non-degradable polyurethanes as permanent structures not meant to be remodeled in situ. Additional biodegradable polymeric compositions are known in the art, and exhibit suitable strength and elasticity for use along with, or substituting for the described PEUU.

In aspects, focusing on biomedical usage, polymeric components suitable for the articles described herein are any polymer that is biocompatible and optionally is biodegradable. In certain non-limiting examples, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting examples, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold, where applicable. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting example, the polymer composition comprises a biomacromolecular component derived from an ECM. For example, the polymer composition may comprise collagen so that collagenase, which is present in situ, can degrade the collagen. The polymers used herein may be elastomeric, meaning they change shape on application of a deforming force and substantially return to an original shape when the deforming force is removed.

In another non-limiting example, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

In certain aspects, degradable polymers used to make the articles described herein also release therapeutic agents when they are implanted in and degrade within the patient's body. For example, the individual building blocks of the polymers may be chosen such that the building blocks themselves provide a therapeutic benefit when released in situ through the degradation process. In one example, one of the polymer building blocks is putrescine, which has been implicated as a substance that causes cell growth and cell differentiation. In another aspect, therapeutic agents may be linked using any applicable chemistry, to the polymer composition so that it is released upon degradation of the polymer composition in situ, such as by a linker comprising an ester bond or another biodegradable linkage.

In certain aspects, the biodegradable polymers comprise homopolymers, copolymers, and/or polymeric blends comprising, without limitation, one or more of the following monomers: glycolide, lactide, caprolactone, dioxanone, and trimethylene carbonate. In other aspects, the polymer(s) comprise labile chemical moieties, non-limiting examples of which include esters and anhydrides, which can be useful in, for example and without limitation, controlling the degradation rate of the articles described herein.

Non-limiting examples of a bioerodible polymer useful for tissue growth scaffolds, hydrogels, or particles include: a polyacrylate or polymethacrylate, a polyacrylamide or polymethacrylamide, a polyester, a polyester-containing copolymer, a polyanhydride, a polyanhydride-containing copolymer, a polyorthoester, and a polyorthoester-containing copolymer. In one aspect, the polyester or polyester-containing copolymer is a poly(lactic-co-glycolic) acid (PLGA) copolymer. In other aspects, the bioerodible polymer is selected from the group consisting of poly(lactic acid)

(PLA); poly(trimethylene carbonate) (PTMC); poly(caprolactone) (PCL); poly(glycolic acid) (PGA); poly(glycolide-co-trimethylenecarbonate) (PGTMC); poly(L-lactide-co-glycolide) (PLGA); polyethylene-glycol (PEG-) containing block copolymers; and polyphosphazenes. Additional bioerodible, biocompatible polymers include: a poly(ester urethane) urea (PEUU); poly(ether ester urethane)urea (PEEUU); poly(ester carbonate)urethane urea (PECUU); poly(carbonate)urethane urea (PCUU); a polyurethane; a polyester; a polymer comprising monomers derived from alpha-hydroxy acids such as: polylactide, poly(lactide-co-glycolide), poly(L-lactide-co-caprolactone), polyglycolic acid, poly(dl-lactide-co-glycolide), and/or poly(l-lactide-co-dl-lactide); a polymer comprising monomers derived from esters including polyhydroxybutyrate, polyhydroxyvalerate, polydioxanone, and/or polyglactin; a polymer comprising monomers derived from lactones including polycaprolactone; or a polymer comprising monomers derived from carbonates including polycarbonate, polyglyconate, poly (glycolide-co-trimethylene carbonate), or poly(glycolide-co-trimethylene carbonate-co-dioxanone).

Non-limiting examples of natural bioerodible polymers useful for preparation of tissue growth scaffolds, hydrogels, or particles include proteins, glycosaminoglycans, and polysaccharides, such as, without limitation, cross-linked or non-cross-linked: heparin, alginate (alginic acid), guar gum, carboxymethylcellulose (CMC), hyaluronic acid, pullulan, carrageenan, pectin, acid modified chitosan, xanthan gum, agarose, chitosan, collagen, elastin, cellulose, hyaluronic acid, and gelatin, and a mixture of any of the foregoing. Synthetic and/or natural polymer compositions may be cross-linked by any of a large variety of known crosslinking methods, using any of the large variety of known cross-linkers, for example, gelatin and/or hyaluronan crosslinked with methacrylate to produce methacrylated gelatin and/or hyalyronan, e.g., by photocrosslinking.

Although bioerodible constituents may be preferred, non-bioerodible polymers may be used that either do not erode substantially in vivo or erode over a time period of greater than two years. Compositions such as, for example and without limitation, polytetrafluoroethylene (PTFE), poly (ethylene-co-vinyl acetate), poly(n-butyl methacrylate), poly(styrene-b-isobutylene-b-styrene), and polyethylene terephthalate are considered to be non-bioerodable polymers. Other suitable non-bioerodable polymer compositions are broadly known in the art, for example, in stent coating and transdermal reservoir technologies. The growth scaffolds described herein may comprise a non-erodible polymer composition.

For uses that do not involve tissue engineering or biocompatibility, virtually any polymer composition amenable to the electrospinning process can be used to prepare the filamentous articles, and branched filamentous articles described herein, and any particles, solutions, liquids, etc. may be co-electrodeposited with the filaments.

With respect to polymer synthesis, diamines, diols, and diisocyanates are useful building blocks for preparing certain of the polymer compositions described herein. Diamines as described above have the structure $H_2N-R-NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as poly-caprolactone-PEG copolymers, including polycaprolactone-b-polyethylene glycol-b-polycaprolactone triblock copolymers of varying sizes. Other building blocks for useful diols include, without limitation glycolides (e.g., polyglycolic acid (PGA)), lactides, dioxanones, and trimethylene carbonates. Diisocyanates have the general structure OCN—R—NCO, where "R" is, e.g., an aliphatic or aromatic hydrocarbon or a hydrocarbon comprising aromatic and aliphatic regions. The hydrocarbon may be linear or branched.

For the purpose of illustration, in aspects, the electrospun polymer composition comprises PEUU, PEEUU, PCUU, and/or PECUU, which may be synthesized as follows. PEUU can be manufactured by reacting a diol with a diisocyanate to form a prepolymer and then reacting the prepolymer with a diamine. A non-limiting example of such a PEUU is an elastomeric polymer made from polycaprolactone diol ($M_W$ 2000) and 1,4-diisocyanatobutane, using a diamine chain extender such as putrescine. One non-limiting example or a method for preparing a PEUU polymer is a two-step polymerization process whereby polycaprolactone diol ($M_W$ 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one example, the diamine is putrescine, which is added drop-wise while stirring and allowed to react at room temperature for 18 hours. In one example, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

PEEUU may be made by reacting polycaprolactone-b-polyethylene glycol-b-polycaprolactone triblock copolymers with 1,4-diisocyanatobutane and putrescine. In one non-limiting example, PEEUU is obtained by a two-step reaction using a 2:1:1 reactant stoichiometry of 1,4-diisocyanatobutane:triblock copolymer:putrescine. According to one non-limiting example, the triblock polymer can be prepared by reacting poly(ethylene glycol) and ε-caprolactone with stannous octoate at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

PECUU may be synthesized using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. Polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

In additional aspects, the polymer composition may include polyethylene terephthalate (PET, e.g., DACRON). Of note, PET is less biodegradable than the copolymers described above, and is stiffer. PET scaffolds structures are made essentially in the manner described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other examples, the polymer composition comprises a tyrosine polyarylate (TPA). As with PET, TPA is less biodegradable than the polyurethane copolymers described above, and also is stiffer. TPA scaffolds structures are made essentially in the manner described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, Poly(DTE-co-27.5 DT succinate) is used. TPAs and methods of making TPAs are described, for example, in U.S. Pat. No. 5,216,115 and United States Patent Application Publication No. 2011/0082545, each of which is incorporated herein by reference for its technical disclosure, disclose useful TPAs.

As used herein, the terms "extracellular matrix" and "ECM" refer to a natural composition useful for cell growth. ECM is decellularized or devitalized tissue, and is a complex mixture of structural and non-structural biomolecules, including, but not limited to, proteins, glycosaminoglycans, proteoglycans, antimicrobials, chemoattractants, cytokines, and growth factors, such as collagens, elastins, and laminins. In mammals, ECM often comprises about 90% collagen in its various forms. The composition and structure of ECMs vary depending on the source of the tissue. For example, small intestine submucosa (SIS), urinary bladder matrix (UBM), liver stroma ECM, and dermal ECM each differ in their overall structure and composition due to the unique cellular niche needed for each tissue.

Generally, any tissue source, and therefore any type of extracellular matrix (ECM) can be used to produce ECM products to be implanted with the cell sheet as described herein. ECM materials are prepared, for example, from decellularized or devitalized ECM material, that optionally has not been dialyzed. ECM materials are broadly-known, and are commercially-available in many forms, and may be prepared from a natural ECM (tissue), or from an in vitro source wherein the ECM is produced by cultured cells and comprises one or more polymeric components (constituents) of native ECM. ECM can be engineered into a variety of three-dimensional structures. In aspects, ECM is isolated from a vertebrate animal, for example, from a warm blooded mammalian vertebrate including, but not limited to, human, monkey, pig, cow, horse, or sheep. The ECM may be derived from any organ or tissue, including without limitation, nerve tissue, connective tissue, urinary bladder, intestine, liver, heart, esophagus, spleen, cartilage, meniscus, bone, stomach, and dermis. Tissue for preparation of ECM as described herein may be harvested in any useful manner. The ECM can comprise any portion or tissue obtained from an organ, including, for example and without limitation, and where relevant, submucosa, epithelial basement membrane, tunica propria, etc. The ECM material may take many different forms, though in the context of chordae tendineae repair, is a sheet, tube, bundled fiber, cylinder, or chordae tendineae-shaped, and affixed in place at the site of implantation using, for example and without limitation, a medically acceptable adhesive or sutures.

ECM material is may be decellularized, disinfected, sterilized, and/or dried by any useful method. The ECM material can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be crosslinked by treatment with glutaraldehyde, but this treatment substantially alters the material such that it is slowly resorbed or not resorbed at all and incites a different type of host remodeling which more closely resembles scar tissue formation or encapsulation, rather than constructive remodeling. Cross-linking of the protein material can also be induced with carbodiimide or dehydrothermal or photooxidation methods. Often, ECM is disinfected by immersion in 0.1% (v/v) peracetic acid (a), 4% (v/v) ethanol, and 96% (v/v) sterile water for 2 h. The decellularized tissue is then washed twice for 15 min with PBS (pH=7.4) and twice for 15 min with deionized water.

Commercially available ECM materials derived from small intestinal submucosa or SIS include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton, Mass.). In another example, the ECM material is derived from dermis. Commercially available preparations include, but are not limited to Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another example, the ECM is derived from urinary bladder. Commercially available preparations include, but are not limited to UBM (Acell Corporation; Jessup, Md.).

ECM gels can be made by any useful method. In its broadest sense, to produce an ECM gel according to one non-limiting example, ECM-derived scaffold materials, e.g., decellularized or devitalized tissue, are comminuted and solubilized to form a hydrogel. In one example, the solubilized hydrogel is not dialyzed. In aspects, solubilization may be achieved by digestion with a suitable acid protease, such as pepsin, under acidic conditions. In one non-limiting aspect, decellularized tissue is lyophilized, comminuted, and is then solubilized with an acid protease. In certain aspects, the decellularized tissue is not dialyzed and/or is not cross-linked (subjected to a cross-linking method) prior to digestion with the acid protease. The acid protease may be, without limitation, pepsin or trypsin, and in one example is pepsin. The decellularized tissue typically is solubilized at an acid pH suitable or optimal for the protease, for example, between pH 1.5 and 3, or in a 0.01M HCl solution (pH~2). The solution typically is solubilized for 12-48 hours, depending upon the tissue type, with mixing (stirring, agitation, admixing, blending, rotating, tilting, etc.). Once the decellularized tissue is solubilized, the pH is raised to between 7.2 and 7.8, and according to one example, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution is gelled at temperatures approaching 37° C., typically at any temperature over 25° C., though gelation proceeds much more rapidly at temperatures over 30° C. and as the temperature approaches physiological temperature (37° C.). The method typically does not include a dialysis step prior to gelation, yielding a more-complete ECM-like matrix that typically gels at 37° C. more slowly than comparable collagen or dialyzed ECM preparations.

In one aspect, the filaments are prepared from a synthetic polymeric composition. In another, the polymeric composition combines a synthetic polymer with an ECM gel, such as described in International Patent Application Publication No. WO 2012/024390, or solutions comprising finely comminuted ECM particles, such as powdered ECM. Where the synthetic polymer and ECM gel are mixed, any ratio of biodegradable, elastomeric polymer to ECM gel that shows excellent cellular infiltration, while displaying adequate tensile strength and elasticity may be used, for example, a useful ratio of polymer to gel ranges from 70%-85%:15%-30%, including increments therebetween. This can be achieved, for example, by codepositing the biodegradable, elastomeric polymer by electrospinning, and the ECM gel by electrospraying, as described above, for example, in FIG. 1. See, e.g., United States Patent Application Publication No. 2008/0260831, incorporated herein by reference for its technical disclosure. (See also, Stankus et al., Hybrid nanofibrous scaffolds from electrospinning of a synthetic biodegradable elastomer and urinary bladder matrix, J Biomater. Sci. Polym. Ed. (2008) 19(5):635-652.) In the Stankus article, PEUU was mixed with solubilized UBM ECM and was electrospun.

In aspects, the electrodeposited, fiber-forming polymer composition comprises a biomacromolecular component derived from an ECM, or the biomacromolecular component derived from an ECM is electrosprayed or otherwise electrodeposited with a separately-electrodeposited fiber-forming polymer composition. For example, the electrodeposited composition may comprise the biomacromolecule collagen so that collagenase, which is present in situ, can degrade the collagen. As an example, the polymer composition may comprise one or both of a collagen and an elastin. Collagen is a common ECM component and typically is degraded in vivo at a rate faster than many synthetic bioerodable polymers. Therefore, manipulation of collagen content in the polymer composition can be used as a method of modifying bioerosion rates in vivo. Collagen may be present in the polymer composition in any useful range, including, without limitation, from about 2% wt. to about 95% wt., for example, in the range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting example, collagen and elastin are present in approximately equal amounts in the polymer composition. In another example, the sum of the collagen and elastin content in the polymer composition is in any useful range, including, without limitation, from about 2% wt. to about 95% wt., for example, in the range of from about 25% wt. to about 75% wt., inclusive of all ranges and points therebetween, including from about 40% wt. to about 75% wt., including about 75% wt. and about 42.3% wt.

As can be appreciated by those of ordinary skill in the art, multiple, different polymer compositions can be mixed together in a suitable solvent in one reservoir and concurrent electrodeposited from a single nozzle, and, therefore, as a single fiber. In another aspect, different polymer compositions are provided in different reservoirs, and are deposited independently from different nozzles concurrently, or at different times and rates. In one aspect, synthetic and biological polymer compositions are mixed in a suitable solvent and are electrodeposited concurrently in one stream from a single nozzle. In another aspect, the synthetic and biological polymer are electrodeposited independently from different reservoirs and nozzles.

In another example, at least one therapeutic agent is added to the article described herein before it is implanted in the patient or otherwise administered to the patient. Generally, the therapeutic agents include any substance that can be coated on, embedded into, absorbed into, adsorbed to, chemically linked to with a labile or digestible bond, or otherwise attached to or incorporated onto or into the structure or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another example, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain aspects, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), Human Vascular Endothelial Growth Factor-165 (hVEGF$_{165}$), Vascular endothelial growth factor A (VEGF-A), Vascular endothelial growth factor B (VEGF-B), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain aspects, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain aspects, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin; nitro-fatty acids, such as nitro-oleic acid or nitro-conjugated linoleic acid. Other drugs that may promote wound healing and/or tissue regeneration may also be included.

In one aspect, articles described herein are prepared by electrospinning of a biodegradable, elastomeric polymer, and concurrent deposition of an ECM gel, a blood product, media, saline, an isotonic buffer, or any other suitable liquid or gel, by spraying, e.g., by physically spraying or by electrospraying. Other compounds or components may be incorporated into a structure as described herein by any method, including absorption, adsorption, mixing, etc. Blood products include, without limitation, blood, serum, plasma, platelet-rich plasma, and may be, for example, allogeneic or autologous, for example human for use in humans, or the blood product is prepared from blood of a patient into whom the article is to be implanted.

In aspects, the polymer matrix, as deposited or formed, is porous. As used herein, the term "porosity" refers to a ratio between a volume of all the pores within the electrodeposited polymer matrix and a volume of the whole electrodeposited polymer matrix. Pores may be filled with liquid, gel, and/or cells in wet-elecrodeposited matrices. For instance, a polymer matrix with a porosity of 85% would have 85% of its volume containing pores and 15% of its volume containing the polymer. In certain non-limiting examples, the porosity of the structure is at least 60%, 65%, 70%, 75%, 80%, 85%, or 90%, or increments therebetween. In another non-limiting example, the average pore size of the structure is between 0.1 and 300 microns, 0.1 and 100 microns, 1-25 microns, including increments therebetween. For example and without limitation, a structure that acts as a barrier to bacteria and other pathogens may have an average pore size of less than 0.5 microns or less than 0.2 microns. Because the structures described herein are manufactured by electrospinning, it is often advantageous to adjust the pore size or degree of porosity by varying the polymer concentration of the electrospinning solution, by varying the spinning distance from the nozzle to the target deposition axis (the axis between the tips of the opposing target electrodes), the polymer Mw, the target-nozzle voltage gap, and/or any other factor that would alter porosity during the electrodeposition process. For example and without limitation, the average pore size may be increased by increasing the amount of polymeric components within the suspension used for electrospinning, which results in larger fiber diameters and, therefore, larger pore sizes. In another non-limiting example, the average pore size can be increased by increasing spinning distance from the nozzle to the target deposition axis, which results in less adherence between fibers and a looser matrix. Where ECM gel or a liquid is co-deposited during the electrospinning, many of the pores (that is a large percentage of the pores or interstices) in the deposited polymer are filled with the ECM gel.

Example 1—Preparation of Filament by Mandrel-Less Electrospinning

Figure 4:
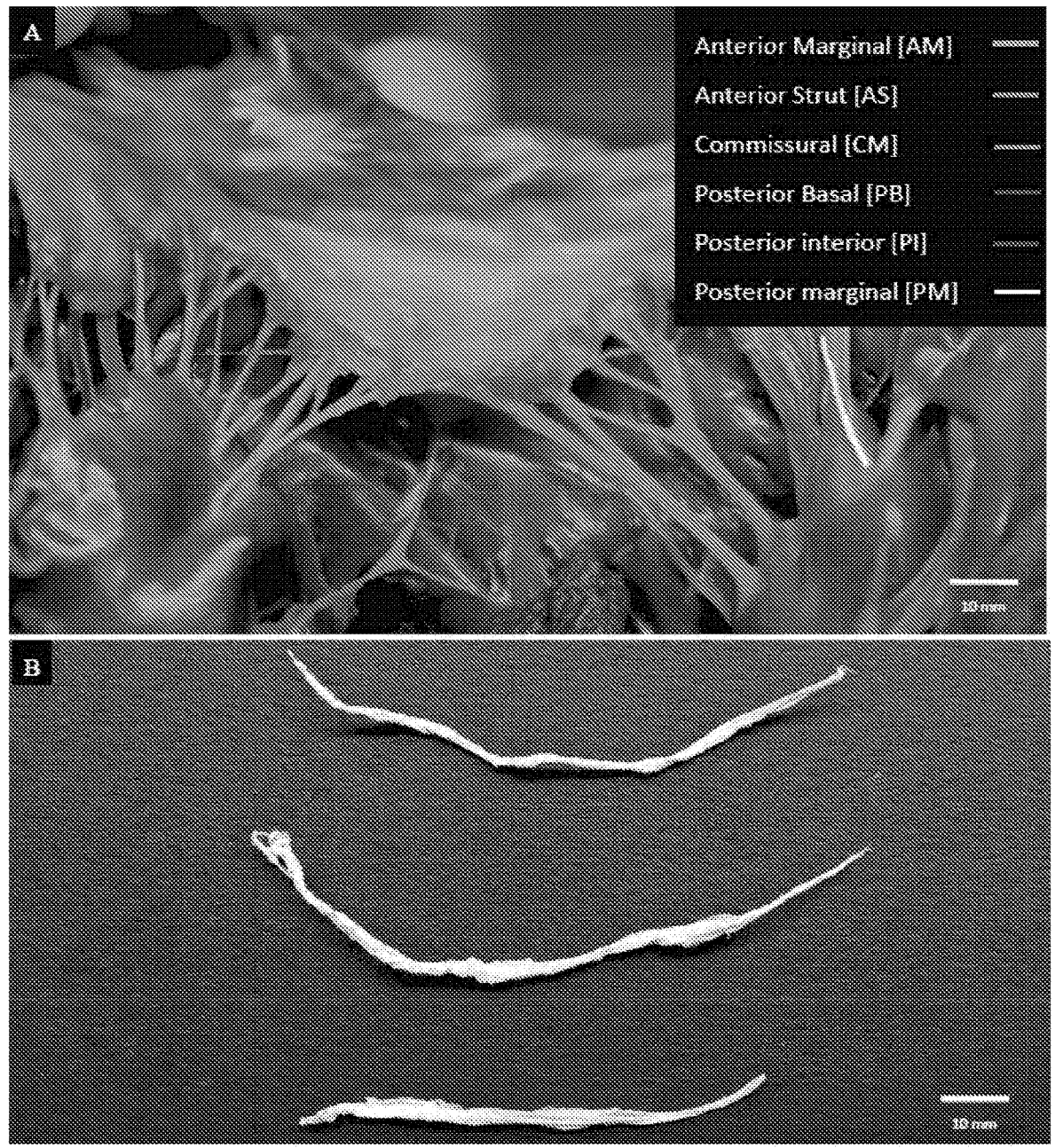
FIG. 4: Native porcine chordae tendineae (A) (panel (A)) compared with the engineered chordae made of PEUU (B).
Figure 5:
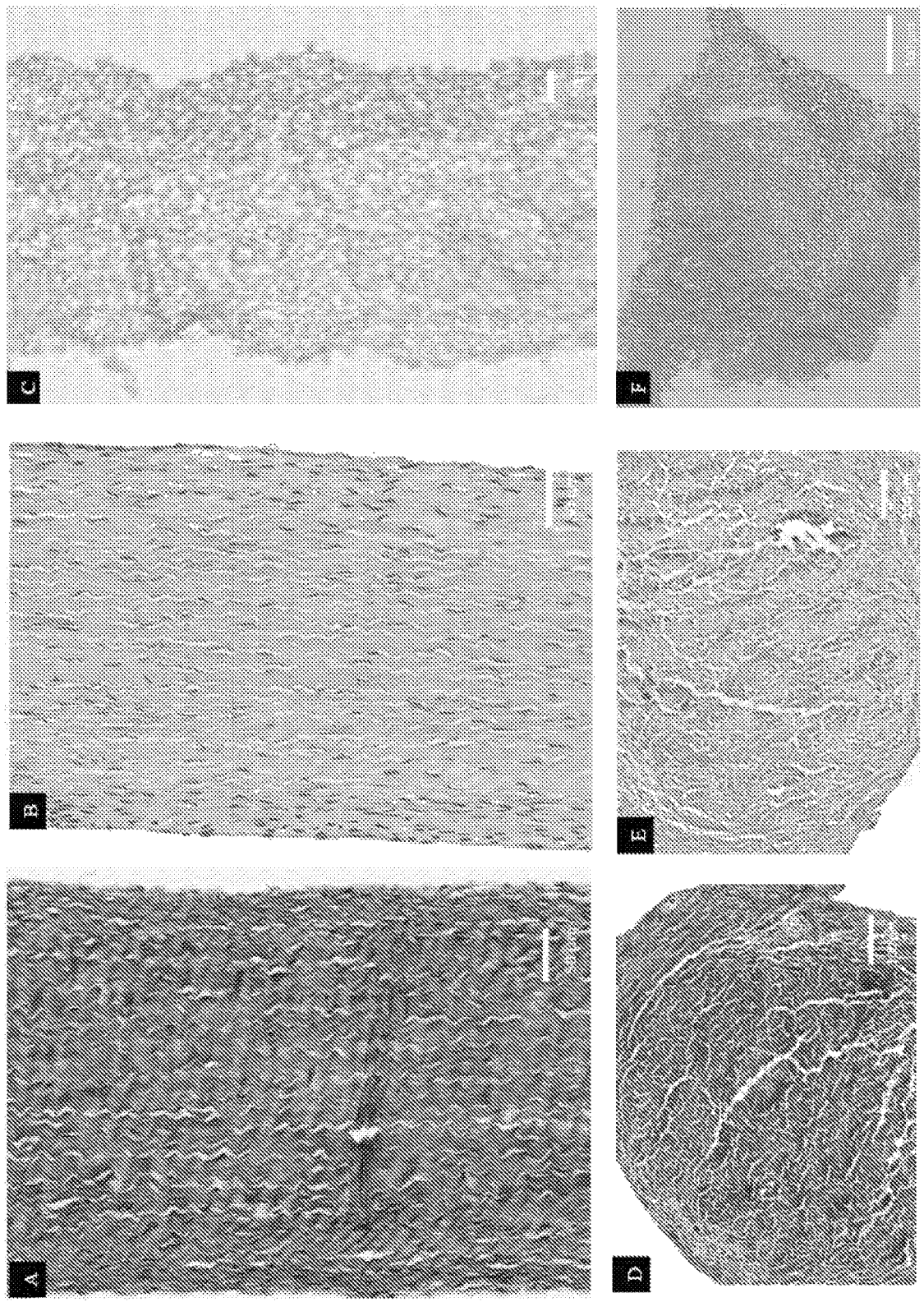
FIG. 5: bright field images comparison of (A) longitudinal porcine anterior marginal chorda tendineae, MT staining; (B) longitudinal anterior marginal chorda tendineae, H&E stain; and (C) longitudinal PEUU engineered chorda H&E stained and their respectively cross section reported in (D), (E), and (F).
Figure 6A:
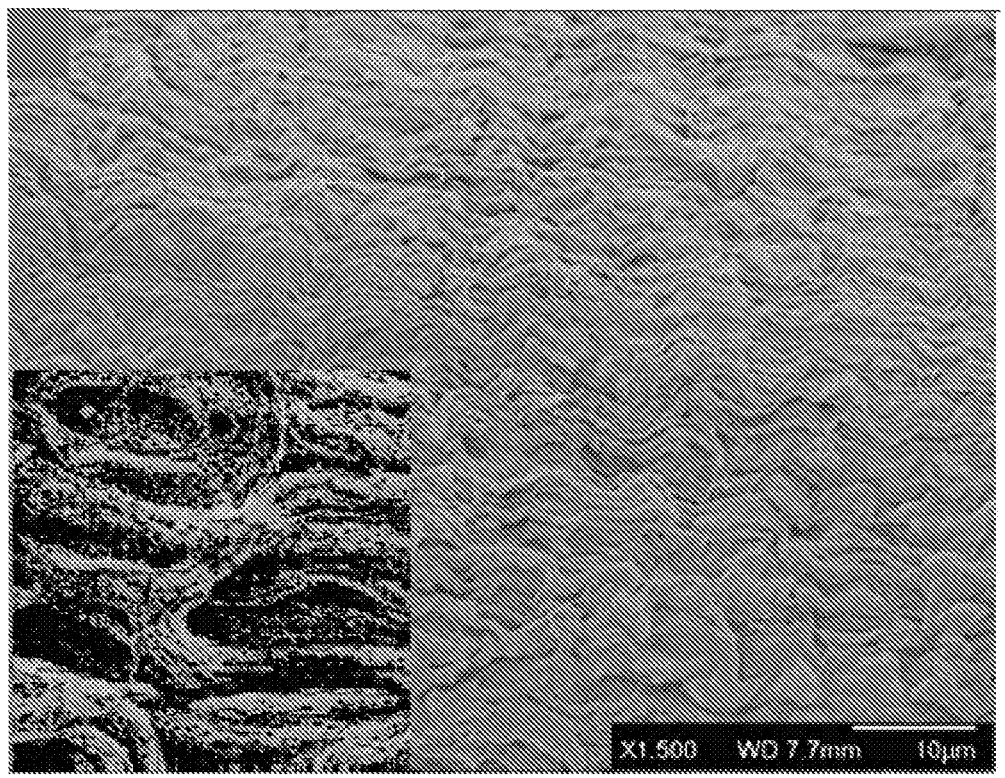
FIGS. 6A-6D.
Figure 6B:
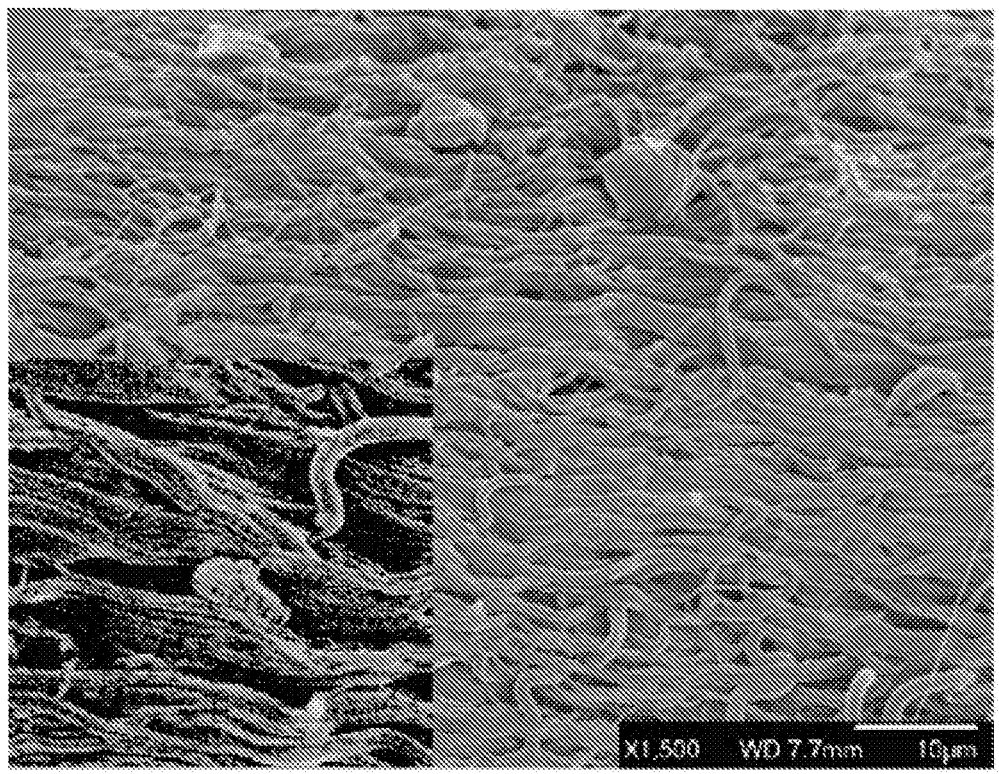
Figure 6C:
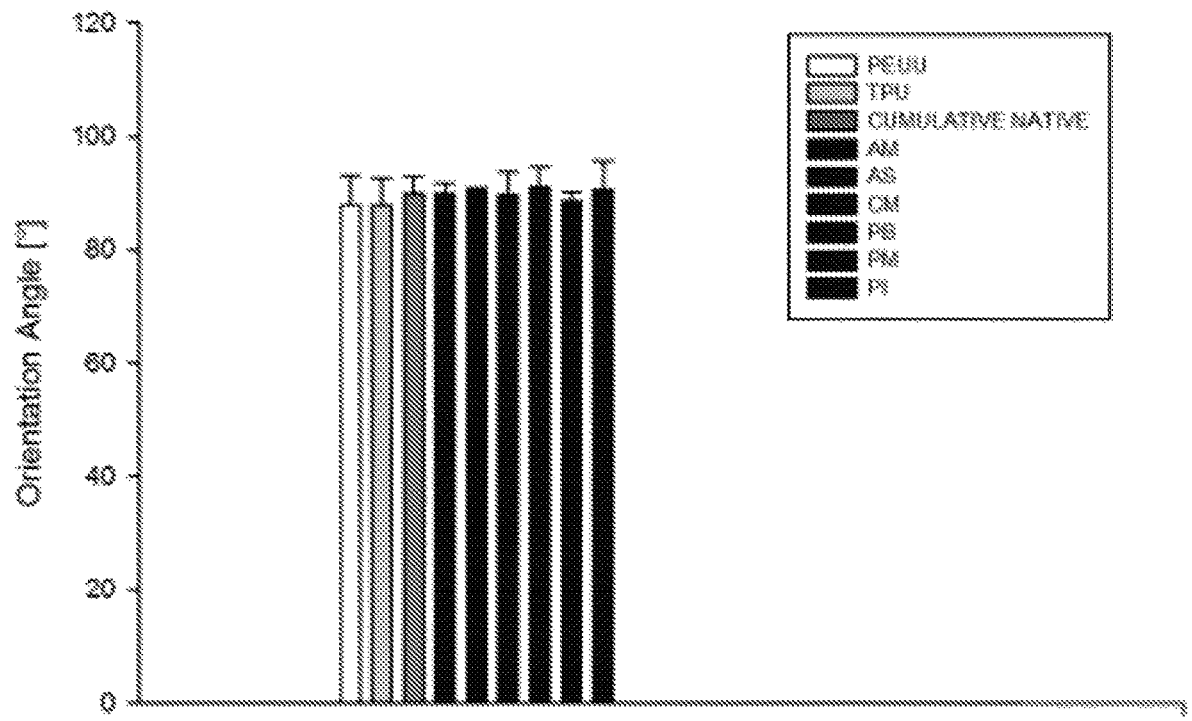
Figure 6D:
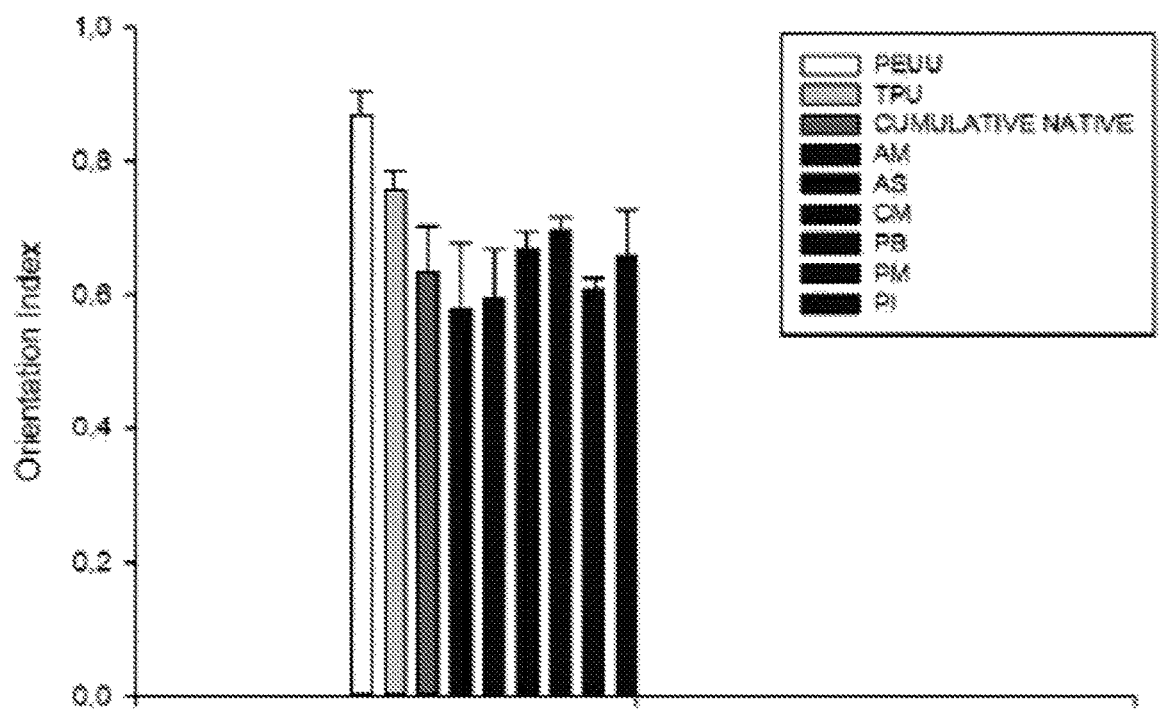
Figure 7:
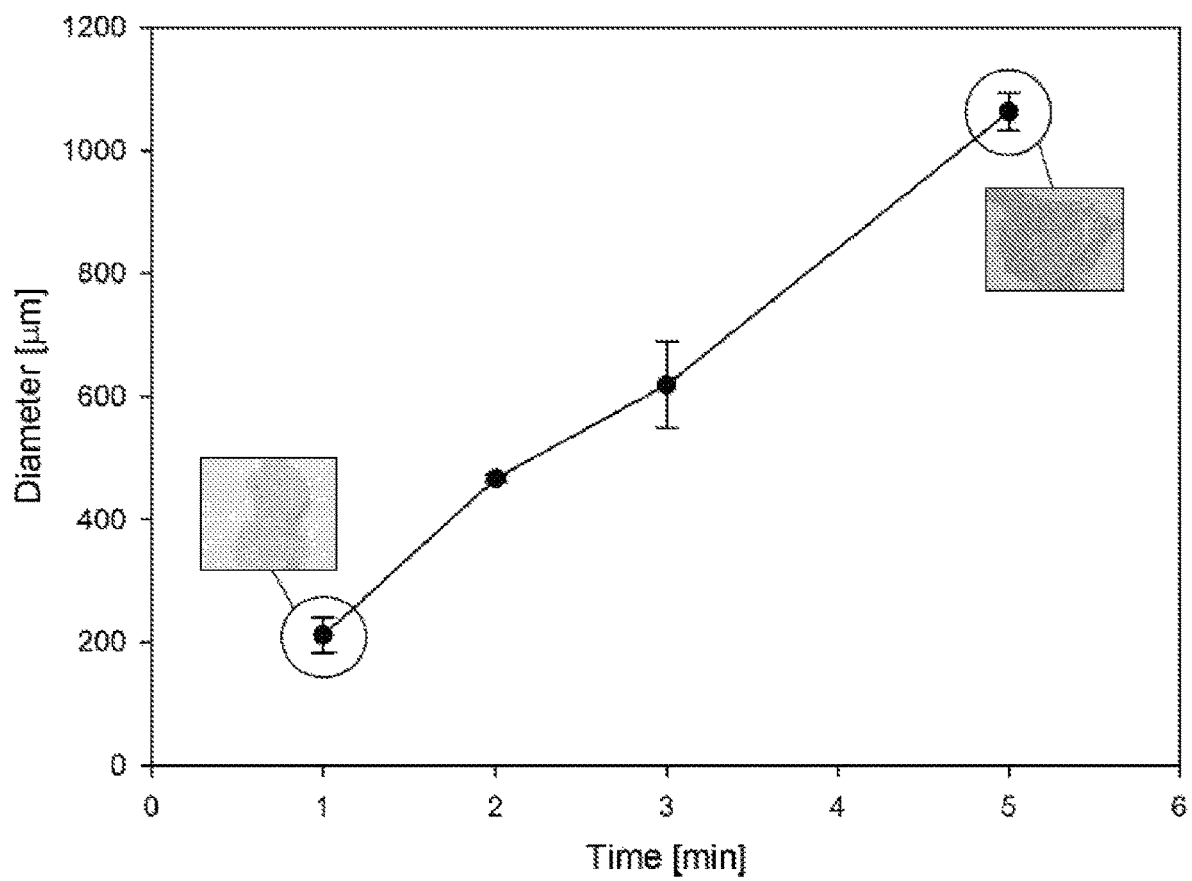
FIG. 7: Thickness versus fiber deposition time characterization. Cross section evaluated via bright field microscopy have been reported respectively at t=1 min; t=3 min; t=5 min.
Figure 8A:
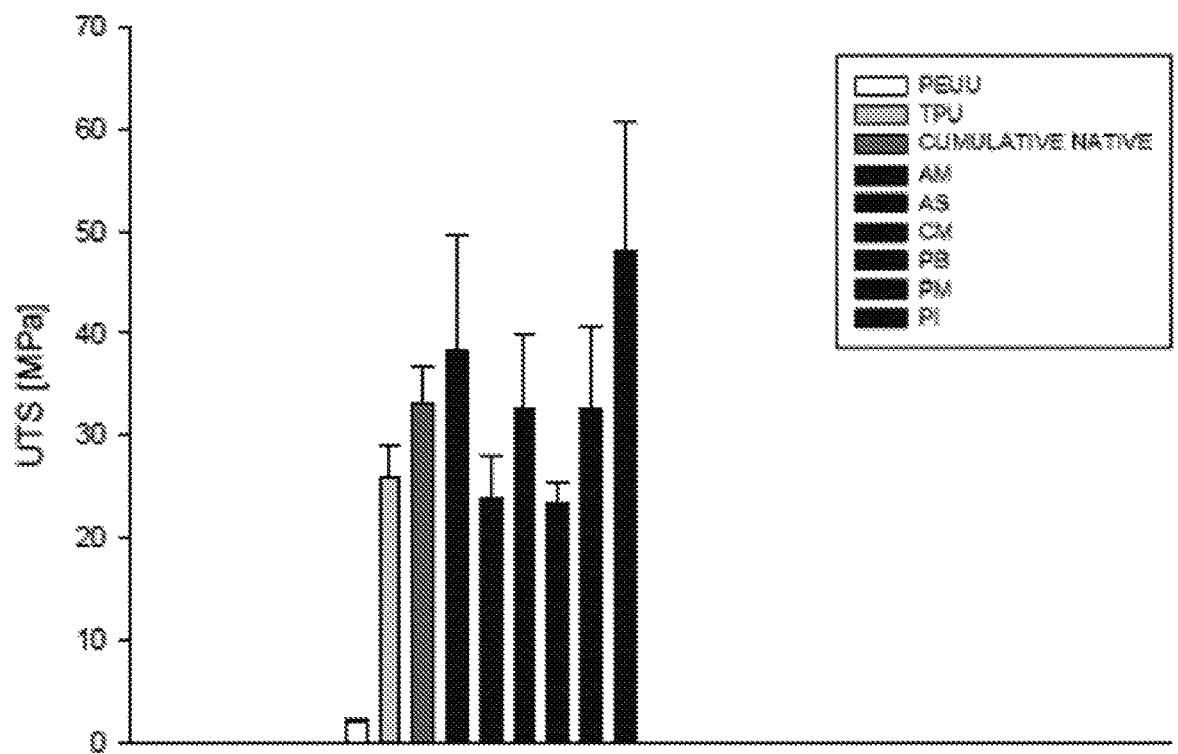
FIGS. 8A-8D: Mechanical properties of native and engineered chordae tendineae.
Figure 8B:
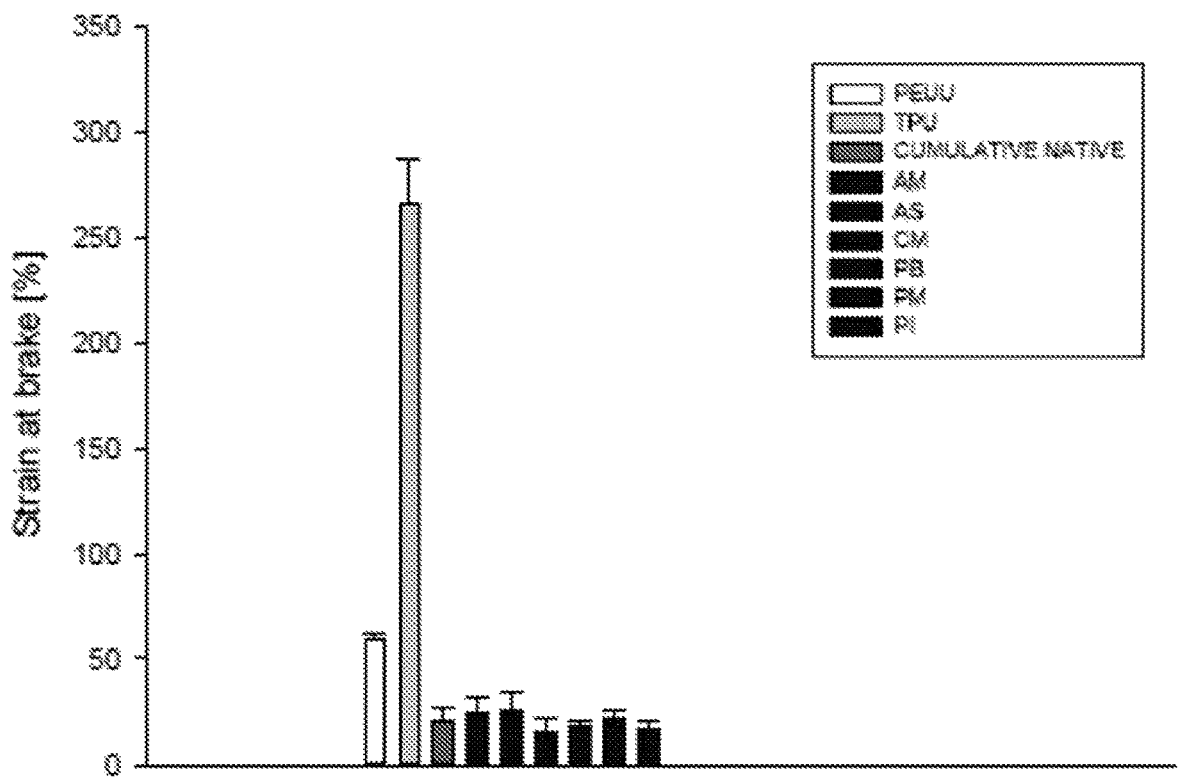
Figure 8C:
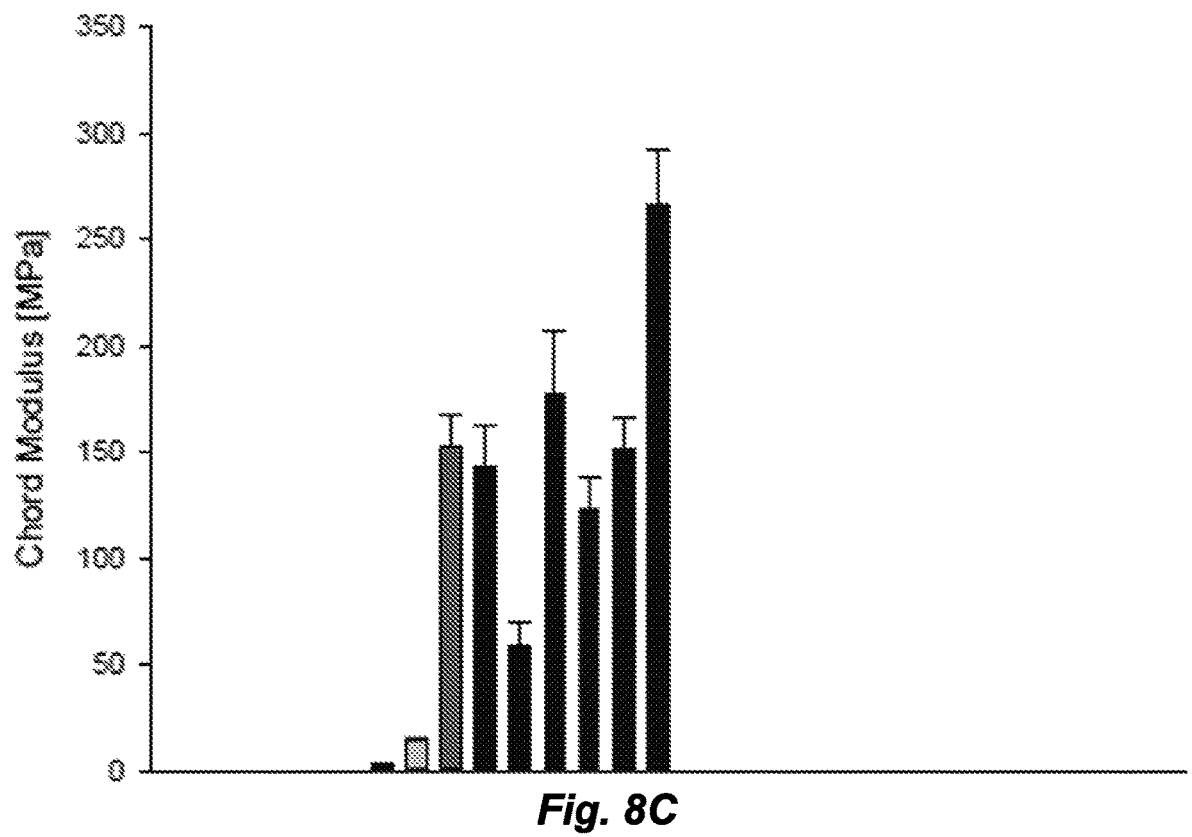
Figure 8D:
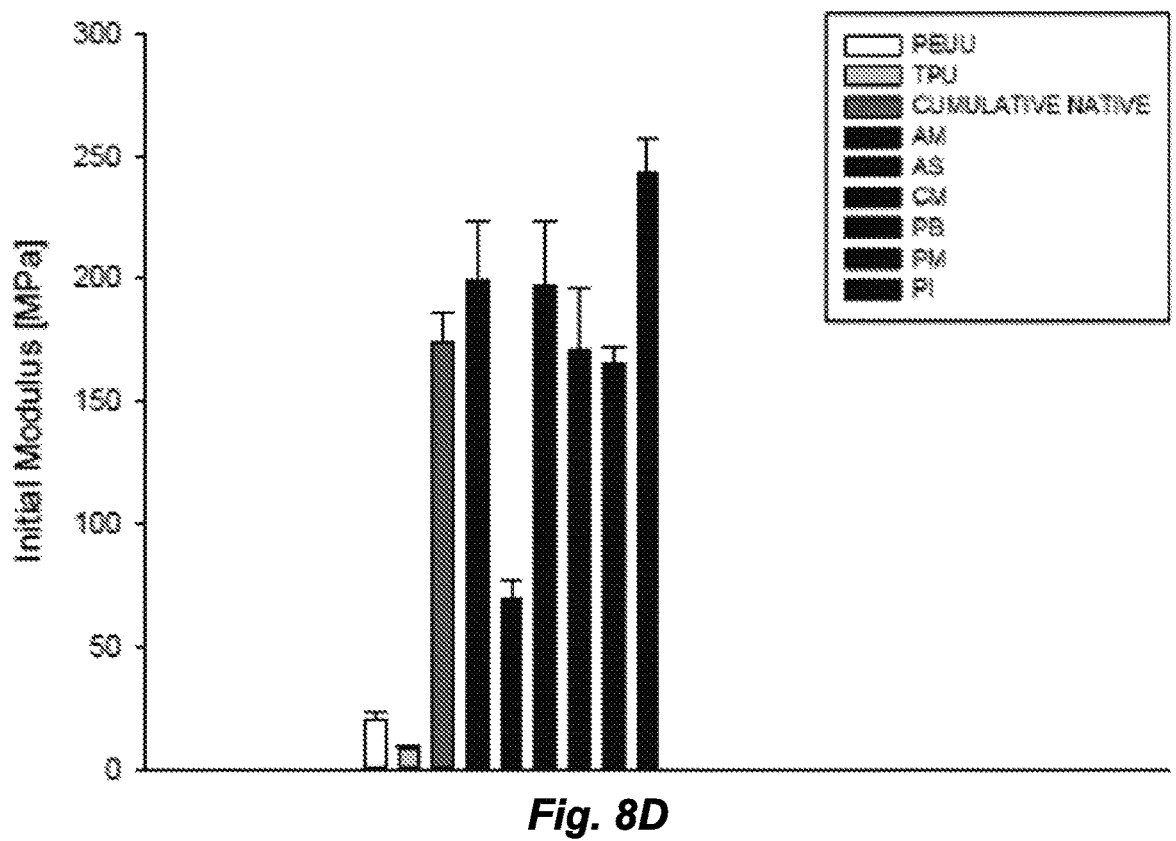

Using a prototype system as described above, PEUU fiber-based chorda with length spanning from 2 cm to 6 cm, with micro-fibers diameters of 0.1-10 µm. An example of a poly(ester urethane) urea (PEUU) chordae tendineae is provided in FIG. 4. Chordae tendineae can be electrospun from a variety of materials, including both degradable or non-degradable polymers. Degradable PEUU was synthesized from polycaprolactone diol (PCL; M$_w$=2000 g/mol, Sigma), 1,4-diisocyanatobutane (BDI, Sigma), and putrescine (Sigma), with a 1:2:1 molar ratio of PCL:BDI:putrescine. The synthesis was carried out in a three-necked round bottomed flask with argon protection in a two-step solution polymerization process. In the first step, PCL diol was completely dissolved in dimethyl sulfoxide (DMSO) before the addition of BDI to the solution. Stannous octoate was then added dropwise, and the reaction was allowed to proceed for 3 h in a 70° C. oil bath. After cooling to room temperature, putrescine dissolved in DMSO was added dropwise to the solution. The reaction proceeded at 50° C. for 1 h before the polymer was precipitated in cool deionized water, followed by drying under vacuum for 2 days at 60° C. For electrospun processing, PEUU was dissolved in 1,1,1,3,3,3-hexafluoroisopropanol (HFIP, Oakwood Products) for a 12% w/v solution. Non-degradable Tecoflex™ thermoplastic polyurethane (TPU, Lubrizol) was used, as purchased, and a 6% w/v solution with HFIP as the solvent was used for electrospinning. Parameters for this application were: constant flow rate of 1.5 ml/h, target voltage varied from +9 to +11 kV, polymer solution voltage varied from −4 to −6 kV, gap distance between the electrodes varied from 2.5 to 5 cm, and gap distance between the spinneret nozzles and the electrodes varied from 6 to 8 cm. Depending on the desired thickness of the chordae tendineae, a deposition time of 1 and 5 minutes was used. FIG. 4 compares engineered chordae (B) and native chordae (A), illustrating similarity in size. FIG. 5 illustrates the similarity between native chordae tissue and the material produced by the electrospinning method according to the methods described herein. FIGS. 6A-6D show in a microscopic level the remarkable similarity between native chorda and engineered chorda prepared from PEUU according to the methods described herein. As can be seen in FIG. 7, thickness of the deposited fiber increases linearly over electrospinning time. Prior methods, such as in W. E. Teo, S. Ramakrishna, Electrospun Fibre Bundle Made of Aligned Nanofibres Over Two Fixed Points, Nanotechnology 16:1878-1879 (2005), depict non-linear deposition using two blades as target electrodes.

Mechanical properties of the native and engineered chorda were tested, including tensile strength, strain at break, elastic modulus, and initial elastic modulus (FIGS. 8A-8D).

Example 2—Preparation of Bifurcated Prosthetic Chordae Tendineae

Figure 9:
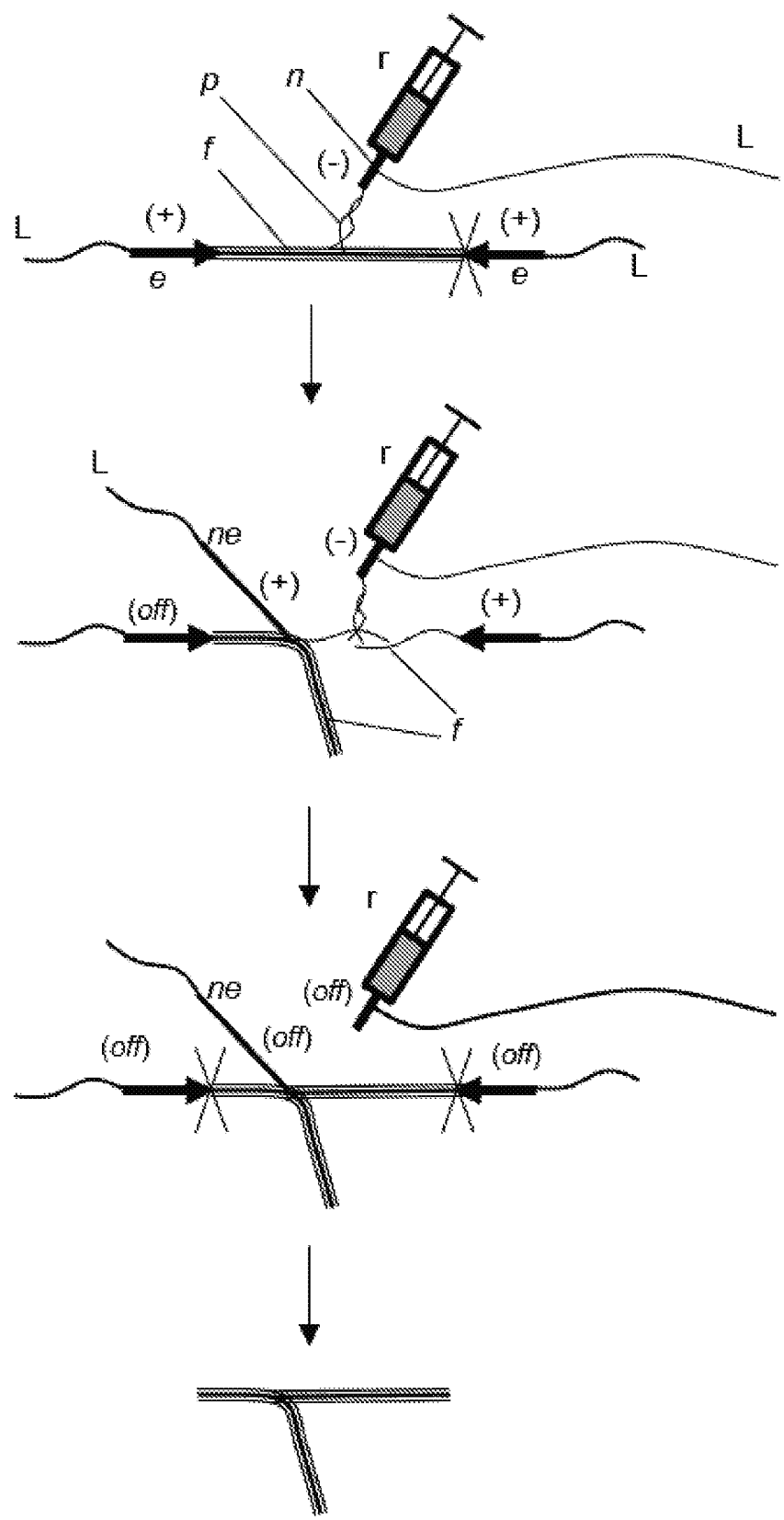
FIG. 9 depicts schematically preparation of a branched filament.

FIG. 9 depicts schematically one aspect of the invention in which a branched fiber is prepared, to mimic branching of chordae. In this method a polymer reservoir r is provided, which is depicted as a medical syringe. The syringe includes a metal nozzle n, which can be a typical hypodermic needle, cannula, or metallic tube. Polymer p is fed from the reservoir r by depressing the plunger of the syringe, for example, manually or by use of a syringe pump as are broadly-available commercially, reservoir r can be any suitable vessel, such as a flask, bottle, container, etc., and polymer can be transferred through the nozzle n by any suitable mechanism, such as gravity feed or by use of a pump, such as a peristaltic pump which, like a syringe pump, can accurately feed the polymer through the nozzle n at acceptable, controlled, and or programmable/automatable rates. Supply of polymer p to the system can be monitored and/or controlled by use of any fluidics systems, including elements such as valve(s) and flow rate sensor(s), as are broadly-known. Polymer p is electrospun between electrodes e as described herein. Nozzle n is depicted as a cathode-having a negative charge, and target electrodes e are depicted as anodes, having a positive charge, but the charges may be reversed, or even simply different—so long as polymer p is deposited between the target electrodes e.

Once a fiber f of adequate thickness is deposited between electrodes e, one end of the fiber f is detached from one of the electrodes e, as depicted by the "X".

Figure 10:
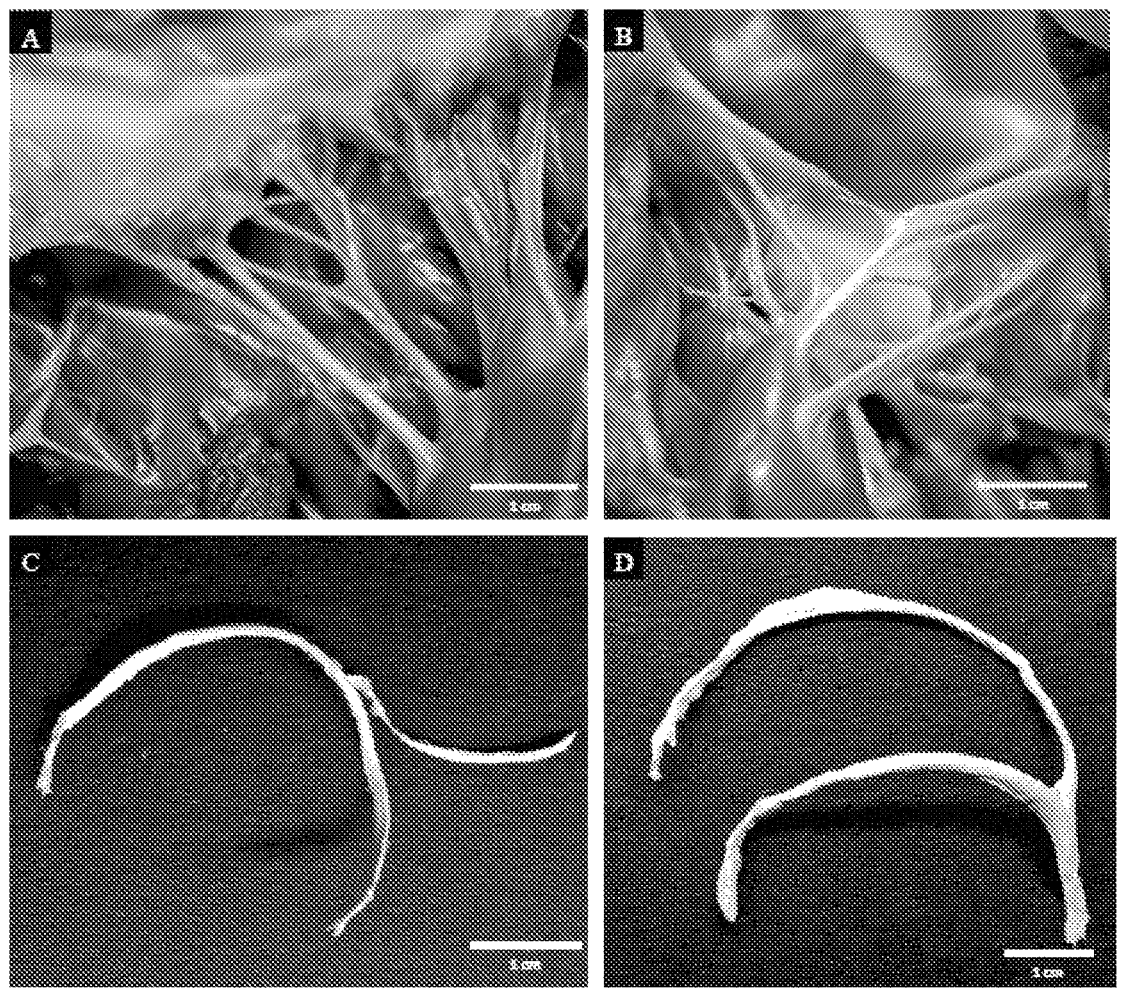
FIG. 10: Capacity to create native-like bifurcation. Comparison between A-B native bifurcated chordae tendineae. C-D engineered chordae with bifurcation obtained as sequential processing of chordae produced according to the protocol in FIG. 9.

Once detached from the electrode, a needle electrode ne, e.g., as shown in FIG. 2, is inserted into the fiber f at a desired branch point, and the electrode e to which the fiber f remains adhered is turned off (optionally), and the needle electrode ne is charged with a similar charge to the other electrode e. Polymer p is then deposited between the needle electrode ne and the electrode e that remains on, producing a branched fiber f, which is then detached from the apparatus. In FIG. 9, positioning stages and other components of the system not necessary for understanding the process are omitted for clarity. Any step, such as insertion of the needle electrode e, cutting the fiber f from the electrodes, etc. can be readily automated by one of ordinary skill. The above process can be repeated to add multiple branches. FIG. 10 depicts native chordae, including branches (Panels (A) and (B)), and engineered chordae ((C) and (D)) produced by sequential deposition of the branch on a nascent fiber.

Example 3—Attachment of Prosthetic Chordae Tendineae to Prosthetic Heart Valve

The filaments, e.g., prosthetic tendons or ligaments, such as chordae tendineae, can be effectively attached to native tissue or other prosthetic devices, such as a prosthetic heart valve. A prosthetic chordae tendineae prepared as described above was successfully solvent welded to an engineered, polymeric mitral valve.

As can be seen in the figures, the voltage generated by the two facing target electrodes induces deposition of highly aligned microscopic fibers which macroscopically will span the space between the target electrodes. The article produced by the described system and method duplicates native tissue anatomy, and function, structure, and mechanics of the chordae prototypes have been characterized and compared.

The following clauses describe various aspects of the invention:

1. A mandrel-less electrodeposition system for use in preparing a filament comprising:
   two static or rotating target electrodes having opposing, spaced-apart tips electrically-connected to an electrical power source, the opposing tips of the electrodes defining a deposition target axis;
   a nozzle electrically-connected to a second electrical power source and spaced apart from the target electrodes and the deposition target axis; and
   a reservoir configured to deliver a polymer composition through the nozzle and to the deposition target axis.
2. The system of clause 1, wherein the nozzle has a first electrical charge, and the target electrodes have a second electrical charge different from the first electrical charge that produces an electric field (voltage gap) that causes fibers of a polymer composition deposited through the nozzle into the target deposition axis to align along the target deposition axis between the electrodes.
3. The system of clause 1, wherein the nozzle has a first electrical charge, and the target electrodes have a second electrical charge of opposite polarity from the first electrical charge (that is, the first electrical charge is a positive charge, and the second electrical charge is a negative charge, or vice versa).
4. The system of clause 1, further comprising a needle electrode, for example an electrode including an elongated tip portion, for example having a diameter of 1 mm or less, electrically-connected to an electrical power source and configured for insertion into a fiber formed along the target deposition axis.
5. The system of clause 1, wherein the polymer composition is biocompatible.
6. The system of clause 1, wherein the polymer composition is bioerodible.
7. The system of clause 1, wherein the polymer composition comprises one or more of: glycolide, lactide, caprolactone, dioxanone, and/or trimethylene carbonate monomers.
8. The system of clause 1, wherein the polymer composition comprises: a poly(ester urethane) urea (PEUU), a poly(ether ester urethane)urea (PEEUU), a poly(ester carbonate)urethane urea (PECUU), a poly(carbonate)urethane urea (PCUU), a polylactide, a poly(lactide-co-glycolide), a poly(L-lactide-co-caprolactone), a polyglycolic acid, a poly(DL-lactide-co-glycolide), a poly(L-lactide-co-L-lactide), a polyester, a polyhydroxybutyrate, a polyhydroxyvalerate, a polydioxanone, a polyglactin, a lactone, a polycaprolactone, a polycarbonate, a polyglyconate, a poly(glycolide-co-trimethylene carbonate), a poly(glycolide-co-tri methylene carbonate-co-dioxanone), or a polyurethane.

9. The system of clause 1, wherein the target electrodes rotate about the deposition target axis.

10. The system of clause 9, wherein the target electrodes rotate synchronously about the deposition target axis.

11. The system of clause 1, wherein the target electrodes do not rotate about the deposition target axis.

12. A method of making a filament, comprising: feeding a first polymer composition through a first nozzle having a first electrical charge into a target deposition axis defined by spaced-apart tips of a first target electrode and a second target electrode, the first and second target electrodes having a different electrical charge from the first electrical charge that produces an electric field (voltage gap) that causes fibers of the polymer composition to align along the target deposition axis between the target electrodes, thereby forming a primary filament between the target electrodes.

13. The method of clause 12, further comprising:
    detaching the primary filament from the first target electrode;
    inserting a tip of a needle electrode into the primary filament;
    feeding a second polymer composition that is the same as or different from the first polymer composition, through a nozzle having a third electrical charge that is the same or different from the first electrical charge, into a second target deposition axis defined by spaced-apart tips of the needle electrode and the first target electrode, the needle electrode and the first target electrode having a fourth electrical charge that is different from the third electrical charge and that is the same or different from the second electrical charge and produces an electric field that causes the second polymer composition to align along the second target deposition axis to form a filament branch attached to the primary filament between the needle electrode and the first target electrode.

14. The method of clause 12 or 13, wherein the second polymer composition and the nozzle having the third electrical charge are the same polymer composition and nozzle as the first polymer composition and the nozzle having the first electrical charge.

15. The method of clause 12 or 13, wherein filament is a prosthetic tendon.

16. The method of clause 12 or 13, wherein filament is a prosthetic ligament.

17. The method of clause 12 or 13, wherein filament is a prosthetic chordae tendineae.

18. The method of clause 17, wherein the filament is branched.

19. The method of clause 17 or 18, further comprising attaching the prosthetic chordae tendineae to a prosthetic heart valve, such as by suturing or solvent welding.

20. The method of clause 12, further comprising rotating the filament as it is being formed.

21. The method of clause 12, wherein the polymer composition comprises one or more of: glycolide, lactide, caprolactone, dioxanone, and/or trimethylene carbonate monomers, poly(ester urethane) urea (PEUU), poly(ether ester urethane)urea (PEEUU), poly(ester carbonate)urethane urea (PECUU), poly(carbonate)urethane urea (PCUU), polylactide, poly(lactide-co-glycolide), poly(L-lactide-co-caprolactone), polyglycolic acid, poly(dl-lactide-co-glycolide), poly(l-lactide-co-dl-lactide), polyester, polyhydroxybutyrate, polyhydroxyvalerate, polydioxanone, polyglactin, lactones, polycaprolactone, polycarbonate, polyglyconate, poly(glycolide-co-tri methylene carbonate), poly(glycolide-co-tri methylene carbonate-co-dioxanone), or polyurethane.

22. The method of clause 12, further comprising one or more additional electrodes that, with the first and second target electrodes produce an electric field.

While the present invention is described with reference to several distinct embodiments, those skilled in the art may make modifications and alterations without departing from the scope and spirit. Accordingly, the above detailed description is intended to be illustrative rather than restrictive.

We claim:

1. A mandrel-less electrodeposition system for use in preparing a filament comprising:
    two static or rotating target electrodes having opposing, spaced-apart tips electrically-connected to an electrical power source, the opposing tips of the electrodes defining a deposition target axis;
    a nozzle electrically-connected to a second electrical power source and spaced apart from the target electrodes and the deposition target axis; and
    a reservoir configured to deliver a polymer composition through the nozzle and to the deposition target axis and not wholly onto a physical target surface, wherein the two electrodes and/or the nozzle move or rotate relative to each other during preparation of the filament.

2. The system of claim 1, wherein the nozzle has a first electrical charge, and the target electrodes have a second electrical charge different from the first electrical charge that produces an electric field that causes fibers of a polymer composition deposited through the nozzle into the target deposition axis to align along the target deposition axis between the electrodes.

3. The system of claim 1, wherein the nozzle has a first electrical charge, and the target electrodes have a second electrical charge of opposite polarity from the first electrical charge.

4. The system of claim 1, further comprising a needle electrode, for example an electrode including an elongated tip portion, for example having a diameter of 1 mm or less, electrically-connected to an electrical power source and configured for insertion into a fiber formed along the target deposition axis.

5. The system of claim 1, wherein the polymer composition is biocompatible and/or bioerodible.

6. The system of claim 1, wherein the polymer composition comprises one or more of: glycolide, lactide, caprolactone, dioxanone, and/or trimethylene carbonate monomers.

7. The system of claim 1, wherein the polymer composition comprises: a poly(ester urethane) urea (PEUU), a poly(ether ester urethane)urea (PEEUU), a poly(ester carbonate)urethane urea (PECUU), a poly(carbonate)urethane urea (PCUU), a polylactide, a poly(lactide-co-glycolide), a poly(L-lactide-co-caprolactone), a polyglycolic acid, a poly(DL-lactide-co-glycolide), a poly(L-lactide-co-L-lactide), a polyester, a polyhydroxybutyrate, a polyhydroxyvalerate, a polydioxanone, a polyglactin, a lactone, a polycaprolactone, a polycarbonate, a polyglyconate, a poly(glycolide-co-trimethylene carbonate), a poly(glycolide-co-trimethylene carbonate-co-dioxanone), or a polyurethane.

8. The system of claim 1, wherein the target electrodes rotate synchronously about the deposition target axis.

9. A method of making a filament, comprising:
    feeding a first polymer composition through a first nozzle having a first electrical charge into a target deposition axis and not wholly onto a physical target surface, wherein the target deposition axis is defined by spaced-apart tips of a first target electrode and a second target electrode, and wherein the first nozzle, the first target electrode, and/or the second target electrode are moved or rotated relative to one another as the first polymer composition is fed through the first nozzle, the first and second target electrodes having a different electrical charge from the first electrical charge that produces an electric field (voltage gap) that causes fibers of the polymer composition to align along the target deposition axis between the target electrodes, thereby forming a primary filament between the target electrodes.

10. The method of claim 9, further comprising:

detaching the primary filament from the first target electrode;

inserting a tip of a needle electrode into the primary filament; and feeding a second polymer composition that is the same as or different from the first polymer composition, through a nozzle having a third electrical charge that is the same or different from the first electrical charge, into a second target deposition axis defined by spaced-apart tips of the needle electrode and the first target electrode, the needle electrode and the first target electrode having a fourth electrical charge that is different from the third electrical charge and that is the same or different from the second electrical charge and produces an electric field that causes the second polymer composition to align along the second target deposition axis to form a filament branch attached to the primary filament between the needle electrode and the first target electrode.

11. The method of claim 10, wherein the second polymer composition and the nozzle having the third electrical charge are the same polymer composition and nozzle as the first polymer composition and the nozzle having the first electrical charge.

12. The method of claim 9, wherein filament is a prosthetic tendon, a prosthetic ligament, or a prosthetic chordae tendineae.

13. The method of claim 9, wherein the filament is branched.

14. The method of claim 9, wherein the filament is a prosthetic chordae tendineae, and further comprising attaching the prosthetic chordae tendineae to a prosthetic heart valve, such as by suturing or solvent welding.

15. A method of making a filament, comprising:

feeding a first polymer composition through a first nozzle having a first electrical charge into a target deposition axis and not wholly onto a physical target surface, wherein the target deposition axis is defined by spaced-apart tips of a first target electrode and a second target electrode, and wherein the first and second target electrodes have a different electrical charge from the first electrical charge that produces an electric field (voltage gap) that causes fibers of the polymer composition to align along the target deposition axis between the target electrodes, thereby forming a primary filament between the target electrodes; and rotating the filament as it is being formed.

16. The method of claim 9, wherein the polymer composition comprises one or more of: glycolide, lactide, caprolactone, dioxanone, and/or trimethylene carbonate monomers, poly(ester urethane) urea (PEUU), poly(ether ester urethane)urea (PEEUU), poly(ester carbonate)urethane urea (PECUU), poly(carbonate)urethane urea (PCUU), polylactide, poly(lactide-co-glycolide), poly(L-lactide-co-caprolactone), polyglycolic acid, poly(dl-lactide-co-glycolide), poly (l-lactide-co-dl-lactide), polyester, polyhydroxybutyrate, polyhydroxyvalerate, polydioxanone, polyglactin, lactones, polycaprolactone, polycarbonate, polyglyconate, poly(glycolide-co-trimethylene carbonate), poly(glycolide-co-trimethylene carbonate-co-dioxanone), or polyurethane.

17. The method of claim 9, further comprising one or more additional electrodes that, with the first and second target electrodes produce an electric field.

18. The system of claim 1, wherein the two static or rotating target electrodes are configured such that polymer deposition to the deposition target axis occurs in absence of the physical target surface.

19. The system of claim 1, wherein the target electrodes rotate about the deposition target axis as the filament is being prepared, and/or wherein the polymer composition delivered through the nozzle and to the deposition target axis is rotated as the filament is being prepared.

20. The method of claim 9, further comprising rotating the first and second target electrodes about the deposition target axis as the filament is being formed.

* * * * *

UNITED STATES PATENT AND TRADEMARK OFFICE
CERTIFICATE OF CORRECTION

PATENT NO.         : 11,680,341 B2
APPLICATION NO.    : 16/494797
DATED              : June 20, 2023
INVENTOR(S)        : Antonio D'Amore et al.

It is certified that error appears in the above-identified patent and that said Letters Patent is hereby corrected as shown below:

On the Title Page

Column 1, Assignees, Line 4, delete "Foundation" and insert -- Foundation, Palermo (IT) --

Signed and Sealed this
Thirty-first Day of October, 2023

Katherine Kelly Vidal
*Director of the United States Patent and Trademark Office*